United States Patent
Danho et al.

(10) Patent No.: US 8,299,023 B2
(45) Date of Patent: Oct. 30, 2012

(54) NEUROPEPTIDE-2 RECEPTOR (Y-2R) AGONISTS

(75) Inventors: Waleed Danho, Wayne, NJ (US); David Charles Fry, Langhorne, PA (US); Robert Alan Goodnow, Jr., Gillette, NJ (US); Wajiha Khan, East Hanover, NJ (US); Joseph Swistok, Nutley, NJ (US); Jefferson Wright Tilley, North Caldwell, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 429 days.

(21) Appl. No.: 12/547,076

(22) Filed: Aug. 25, 2009

(65) Prior Publication Data

US 2010/0069307 A1    Mar. 18, 2010

Related U.S. Application Data

(60) Provisional application No. 61/097,621, filed on Sep. 17, 2008.

(51) Int. Cl.
*A61K 38/10* (2006.01)
(52) U.S. Cl. .......... 514/5.2; 514/21.5; 530/327
(58) Field of Classification Search .......... None
See application file for complete search history.

(56) References Cited

U.S. PATENT DOCUMENTS

| | | | |
|---|---|---|---|
| 5,283,317 A | 2/1994 | Saifer et al. | |
| 5,468,478 A | 11/1995 | Saifer et al. | |
| 7,410,949 B2* | 8/2008 | Danho et al. | 514/1.1 |
| 7,642,244 B2* | 1/2010 | Conde-Knape et al. | 514/1.1 |

FOREIGN PATENT DOCUMENTS

| | | |
|---|---|---|
| WO | WO 94/22467 A1 | 10/1994 |
| WO | 2004/103390 | 12/2004 |
| WO | 2005/053726 | 6/2005 |
| WO | WO 2005080424 | 9/2005 |
| WO | 2006/096207 | 9/2006 |
| WO | 2007/065808 | 6/2007 |
| WO | 2007/095443 | 8/2007 |
| WO | 2007/115164 | 10/2007 |

OTHER PUBLICATIONS

Decarr et al, Identification of selective neuropeptide Y2 peptide agonists, Bioorganic & Medicinal Chemistry Letters 17:2 (2007) 538-541 XP00582769.

* cited by examiner

*Primary Examiner* — Christina Bradley
(74) *Attorney, Agent, or Firm* — George W. Johnston; Dennis P. Tramaloni; Samuel H. Megerditchian

(57) ABSTRACT

Provided herein are neuropeptide-2 receptor agonists of the formula (I):

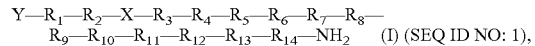

(I) (SEQ ID NO: 1), as well as pharmaceutically acceptable salts, derivatives and fragments thereof, wherein the substituents are as those disclosed in the specification. These compounds, and the pharmaceutical compositions containing them, are useful for the treatment of diseases such as, for example, obesity and diabetes.

5 Claims, No Drawings

SEQUENCE LISTING

```
<160> NUMBER OF SEQ ID NOS: 14

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H or acyl moiety
<220> FEATURE:
<221> NAME/KEY: MOD_RES
<222> LOCATION: (1)..(1)
```

```
<223> OTHER INFORMATION: Ile, Ala, D-Ile, N-methyl Ile, Aib, 1-1Aic, 2-2
      Aic, Ach or Acp
<220> FEATURE:
<221> NAME/KEY: MOD_RES
<222> LOCATION: (2)..(3)
<223> OTHER INFORMATION: This region may encompass 1 to 2 residues
      selected from Lys, Ala, D-Lys, N-methyl Lys, Nle or "Lys Gly"
<220> FEATURE:
<221> NAME/KEY: MOD_RES
<222> LOCATION: (4)..(4)
<223> OTHER INFORMATION: Cba, Cip, HomPqa, Dqa, Pdp, Ppa, Appa, Bqa or
      Pipa
<220> FEATURE:
<221> NAME/KEY: MOD_RES
<222> LOCATION: (5)..(5)
<223> OTHER INFORMATION: Arg, Ala, D-Arg, N-methyl Arg, Phe, 3,4,5-
      Trifluoro Phe or 2,3,4,5,6- Pentafluoro Phe
<220> FEATURE:
<221> NAME/KEY: MOD_RES
<222> LOCATION: (6)..(6)
<223> OTHER INFORMATION: His, Ala, D-His, N-methyl His, 4-MeOApc, 3-Pal
      or 4-Pal
<220> FEATURE:
<221> NAME/KEY: MOD_RES
<222> LOCATION: (7)..(7)
<223> OTHER INFORMATION: Tyr, Ala, D-Tyr, N- methyl Tyr, Trp, Tic, Bip,
      Dip, (1)Nal, (2)Nal, 3,4,5- TrifluroPhe or  2,3,4,5,6- Pentafluoro
      Phe
<220> FEATURE:
<221> NAME/KEY: MOD_RES
<222> LOCATION: (8)..(8)
<223> OTHER INFORMATION: Leu, Ala, D-Leu or N-methyl Leu
<220> FEATURE:
<221> NAME/KEY: MOD_RES
<222> LOCATION: (9)..(9)
<223> OTHER INFORMATION: Asn, Ala or D-Asn
<220> FEATURE:
<221> NAME/KEY: MOD_RES
<222> LOCATION: (10)..(10)
<223> OTHER INFORMATION: Leu or Trp
<220> FEATURE:
<221> NAME/KEY: MOD_RES
<222> LOCATION: (11)..(11)
<223> OTHER INFORMATION: Val, Ala, D-Val or N-methyl Val
<220> FEATURE:
<221> NAME/KEY: MOD_RES
<222> LOCATION: (12)..(12)
<223> OTHER INFORMATION: Thr, Ala or N-methyl Thr
<220> FEATURE:
<221> NAME/KEY: MOD_RES
<222> LOCATION: (13)..(13)
<223> OTHER INFORMATION: Arg, D-Arg or N-methyl Arg
<220> FEATURE:
<221> NAME/KEY: MOD_RES
<222> LOCATION: (14)..(14)
<223> OTHER INFORMATION: Gln or Ala
<220> FEATURE:
<221> NAME/KEY: MOD_RES
<222> LOCATION: (15)..(15)
<223> OTHER INFORMATION: Arg, D-Arg or N-methyl Arg
<220> FEATURE:
<221> NAME/KEY: MOD_RES
<222> LOCATION: (16)..(16)
<223> OTHER INFORMATION: Tyr, D- Tyr or N-methyl Tyr, modified-Tyr, Phe,
      modified-Phe, (1)Nal, (2)Nal, Cha, C-alpha-methyl
      Tyr or Trp
<220> FEATURE:
<223> OTHER INFORMATION: C-term NH2
<220> FEATURE:
<223> OTHER INFORMATION: see specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa
1               5                   10                  15

<210> SEQ ID NO 2
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acyl moiety
<220> FEATURE:
<221> NAME/KEY: MOD_RES
<222> LOCATION: (3)..(3)
<223> OTHER INFORMATION: Cba, Cip, HomPqa, Dqa, Pdp, Ppa, Appa, Bqa or
      Pipa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 2

Ile Lys Xaa Arg His Tyr Leu Asn Trp Val Thr Arg Gln Arg Tyr
1               5                   10                  15

<210> SEQ ID NO 3
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<223> OTHER INFORMATION: C-term NH2

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Pqa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 4

Ile Lys Xaa Arg His Tyr Leu Asn Trp Val Thr Arg Gln Arg Tyr
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                                    peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Cba
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 5

Ile Lys Xaa Arg His Tyr Leu Asn Trp Val Thr Arg Gln Arg Tyr
1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
                                    peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Cip
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 6

Ile Lys Xaa Arg His Tyr Leu Asn Trp Val Thr Arg Gln Arg Tyr
1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
                                    peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: HomPqa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 7

Ile Lys Xaa Arg His Tyr Leu Asn Trp Val Thr Arg Gln Arg Tyr
1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
                                    peptide
<220> FEATURE:
```

```
<223> OTHER INFORMATION: N-term Ac
<220> FEATURE:
<221> NAME/KEY: MOD_RES
<222> LOCATION: (3)..(3)
<223> OTHER INFORMATION: Dqa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 8

Ile Lys Xaa Arg His Tyr Leu Asn Trp Val Thr Arg Gln Arg Tyr
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Pdp
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 9

Ile Lys Xaa Arg His Tyr Leu Asn Trp Val Thr Arg Gln Arg Tyr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Ppa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 10

Ile Lys Xaa Arg His Tyr Leu Asn Trp Val Thr Arg Gln Arg Tyr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
```

```
<221> NAME/KEY: MOD_RES
<222> LOCATION: (3)..(3)
<223> OTHER INFORMATION: Appa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 11

Ile Lys Xaa Arg His Tyr Leu Asn Trp Val Thr Arg Gln Arg Tyr
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Bqa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 12

Ile Lys Xaa Arg His Tyr Leu Asn Trp Val Thr Arg Gln Arg Tyr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: Pipa
<220> FEATURE:
<221> NAME/KEY: MOD_RES
<222> LOCATION: (14)..(14)
<223> OTHER INFORMATION: N-methyl Arg
<220> FEATURE:
<223> OTHER INFORMATION: C-term NH2

<400> SEQUENCE: 13

Ile Lys Xaa Arg His Tyr Leu Asn Trp Val Thr Arg Gln Arg Tyr
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acyl moiety
<220> FEATURE:
<221> NAME/KEY: MOD_RES
<222> LOCATION: (1)..(1)
```

-continued

<223> OTHER INFORMATION: Ile, Ala, D-Ile, N-methyl Ile, Aib, 1-1Aic, 2-2 Aic, Ach or Acp
<220> FEATURE:
<221> NAME/KEY: MOD_RES
<222> LOCATION: (2)..(3)
<223> OTHER INFORMATION: This region may encompass 1 to 2 residues selected from Lys, Ala, D-Lys, N-methyl Lys, Nle or "Lys Gly"
<220> FEATURE:
<221> NAME/KEY: MOD_RES
<222> LOCATION: (4)..(4)
<223> OTHER INFORMATION: Cba, Cip, HomPqa, Dqa, Pdp, Ppa, Appa, Bqa or Pipa
<220> FEATURE:
<221> NAME/KEY: MOD_RES
<222> LOCATION: (5)..(5)
<223> OTHER INFORMATION: Arg, Ala, D-Arg, N-methyl Arg, Phe, 3,4,5-Trifluoro Phe or 2,3,4,5,6- Pentafluoro Phe
<220> FEATURE:
<221> NAME/KEY: MOD_RES
<222> LOCATION: (6)..(6)
<223> OTHER INFORMATION: His, Ala, D-His, N-methyl His, 4-MeOApc, 3-Pal or 4-Pal
<220> FEATURE:
<221> NAME/KEY: MOD_RES
<222> LOCATION: (7)..(7)
<223> OTHER INFORMATION: Tyr, Ala, D-Tyr, N- methyl Tyr, Trp, Tic, Bip, Dip, (1)Nal, (2)Nal, 3,4,5- TrifluroPhe or 2,3,4,5,6- Pentafluoro Phe
<220> FEATURE:
<221> NAME/KEY: MOD_RES
<222> LOCATION: (8)..(8)
<223> OTHER INFORMATION: Leu, Ala, D-Leu or N-methyl Leu
<220> FEATURE:
<221> NAME/KEY: MOD_RES
<222> LOCATION: (9)..(9)
<223> OTHER INFORMATION: Asn, Ala or D-Asn
<220> FEATURE:
<221> NAME/KEY: MOD_RES
<222> LOCATION: (10)..(10)
<223> OTHER INFORMATION: Leu or Trp
<220> FEATURE:
<221> NAME/KEY: MOD_RES
<222> LOCATION: (11)..(11)
<223> OTHER INFORMATION: Val, Ala, D-Val or N-methyl Val
<220> FEATURE:
<221> NAME/KEY: MOD_RES
<222> LOCATION: (12)..(12)
<223> OTHER INFORMATION: Thr, Ala or N-methyl Thr
<220> FEATURE:
<221> NAME/KEY: MOD_RES
<222> LOCATION: (13)..(13)
<223> OTHER INFORMATION: Arg, D-Arg or N-methyl Arg
<220> FEATURE:
<221> NAME/KEY: MOD_RES
<222> LOCATION: (14)..(14)
<223> OTHER INFORMATION: Gln or Ala
<220> FEATURE:
<221> NAME/KEY: MOD_RES
<222> LOCATION: (15)..(15)
<223> OTHER INFORMATION: Arg, D-Arg or N-methyl Arg
<220> FEATURE:
<221> NAME/KEY: MOD_RES
<222> LOCATION: (16)..(16)
<223> OTHER INFORMATION: Tyr, D- Tyr or N-methyl Tyr, modified-Tyr, Phe, modified-Phe, (1)Nal, (2)Nal, Cha, C-alpha-methyl Tyr or Trp
<220> FEATURE:
<223> OTHER INFORMATION: C-term NH2
<220> FEATURE:
<223> OTHER INFORMATION: see specification as filed for detailed description of substitutions and preferred embodiments

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

NEUROPEPTIDE-2 RECEPTOR (Y-2R) AGONISTS

PRIORITY TO RELATED APPLICATIONS

This application claims the benefit of U.S. Provisional Application No. 61/097,621, filed Sep. 17, 2008, which is hereby incorporated by reference in its entirety.

This application is related to U.S. application Ser. No. 11/328,743, filed Jan. 10, 2006, issued as U.S. Pat. No. 7,410,949; provisional application Ser. No. 60/444,840, filed Jan. 18, 2005; and U.S. application Ser. No. 12/136,263, filed Jun. 10, 2008, pending, all of which are expressly incorporated herein by reference.

This application is also related to U.S. application Ser. No. 11/607,230, filed Dec. 1, 2006, pending; and provisional application Ser. Nos. 60/855,249, filed Oct. 30, 2006, and 60/748,071, filed Dec. 7, 2005, all of which are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 20, 2012, is named 24459US1.txt and is 9,880 bytes in size.

FIELD OF THE INVENTION

The invention provides for truncated analogs of $PYY_{3-36}$. The analogs are agonists of neuropeptide-2 receptor and are useful for the treatment of metabolic diseases and disorders, such as, for example, obesity, type 2 diabetes, metabolic syndrome, insulin resistance and dyslipidemia.

All documents cited herein are hereby expressly incorporated herein by reference.

BACKGROUND OF THE INVENTION

Metabolic diseases and disorders are widely recognized as serious health problems for developed countries, having reached epidemic levels in the United States. According to recent studies on obesity, for example, more than 50% of the U.S. population is considered overweight, with more than 25% diagnosed as clinically obese and at considerable risk for heart disease, type 2 diabetes and certain cancers. This epidemic presents a significant burden on the health care system as projected obesity treatment costs of more than $70 billion annually are expected in the U.S. alone. Strategies for treating obesity include reduction of food intake and enhancing the expenditure of energy.

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexogenic agents known and has been shown to play a major role in the regulation of food intake in animals, including humans.

Six neuropeptide Y receptors (NPY), the Y1-, Y2-, Y3-, Y4, and Y5- and Y6-subtypes, have been cloned, which belong to the rhodopsin-like G-protein-coupled 7-transmembrane spanning receptors (GPCR). The NPY Y2 receptor (Y2R) is a 381 amino-acid receptor which inhibits the activation of adenyl cyclase via $G_i$ while displaying low homology with other known NPY receptors. There is a high degree of conservation between rat and human Y2 receptors with 98% amino acid identity.

The Y2R receptor is widely distributed within the central nervous system in both rodents and humans. In the hypothalamus, Y2 mRNA is localized in the arcuate nucleus, preoptic nucleus, and dorsomedial nucleus. In the human brain, Y2R is the predominant Y receptor subtype. Within the arcuate nucleus, over 80% of the NPY neurons co-express Y2R mRNA. Application of a Y2-selective agonist has been shown to reduce the release of NPY from hypothalamic slices in vitro, whereas the Y2 non-peptide antagonist BIIE0246 increases NPY release. These findings support the role of Y2R as a presynaptic autoreceptor that regulates the NPY release and hence may be involved in the regulation of feeding. (Kaga, T. et al., Peptides 22: 501-506 (2001) and King P J et al., Eur J Pharmacol 396: R1-3 (2000)).

Peptide $YY_{3-36}$ ($PYY_{3-36}$) is a 34 amino acid linear peptide having neuropeptide Y2 (NPY2R) agonist activity. It has been demonstrated that Intra-arcuate (IC) or Intra-peritoneal (IP) injection of $PYY_{3-36}$ reduced feeding in rats and, as a chronic treatment, reduced body weight gain. Intra-venous (IV) infusion (0.8 pmol/kg/min) for 90 min of $PYY_{3-36}$ reduced food intake in obese and normal human subjects over 24 hours. These finding suggest that the PYY system may be a therapeutic target for the treatment of obesity. (Batterham R L et al., Nature 418: 650-654 (2002); Batterham R L et al., New Engl J Med 349: 941-948 (2003)). Further, a $Cys^2$-$(D)Cys^{27}$-cyclized version of PYY, in which residues 5-24 were replaced by a methylene-chain of 5 to 8 carbons in length, showed activation of the intestinal PYY receptor, as evidenced by reduced current across voltage-clamped mucosal preparations of rat jejunum. (Krstenansky, et al. in Peptides, Proceedings of the Twelfth American Peptide Symposium. J. Smith and J. Rivier Editors, ESCOM. Leiden Page 136-137).

In addition, recent data have shown that Roux-enY gastric bypass patients have an early and exaggerated increase in PYY levels that may be partly responsible for the early glycemic control and long term weight maintenance demonstrating the importance of this peptide in the pathogenesis of metabolic diseases. Other known actions of PYY include: reduced gastric emptying and delayed gastrointestinal transit that is responsible for improved postprandial glycemic control. Indices of hyperglycaemia such as $HbA_{1C}$ and fructosamine show a dose-dependent reduction after peripheral administration of $PYY_{3-36}$ in animal models of type 2 diabetes. Thus, these results indicate that $PYY_{3-36}$, or pharmaceutically related agonists, may offer a long term therapeutic approach to glycemic and weight control. (Korner et al., J Clin Endocrinol Metabol 90: 359-365 (2005); Chan J L et al., Obesity 14: 194-198 (2006); Stratis C et al., Obes Surg 16: 752-758 (2006); Borg C M et al., Br J Surg 93: 210-215 (2006); and Pittner R A et al., Int J Obes 28: 963-971 (2004)).

A need exists, however, for novel engineered analogs of PYY having lower molecular weight, while possessing equal or better potency and selectivity against Y1, Y4 and Y5 receptors, pharmacokinetic properties and pharmacological properties.

SUMMARY OF THE INVENTION

Provided herein are neuropeptide-2 receptor agonists of formula (I):

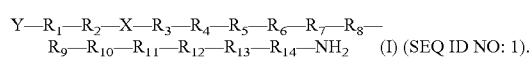

(I) (SEQ ID NO: 1).

The compounds of the invention are preferably useful for treating metabolic diseases and disorders. Such metabolic diseases and disorders include, for example, obesity, diabetes, preferably type 2 diabetes, metabolic syndrome (also known as Syndrome X), insulin resistance, dyslipidemia, impaired fasting glucose and impaired glucose tolerance.

DETAILED DESCRIPTION OF THE INVENTION

In one embodiment of the present invention, provided is a neuropeptide-2 receptor agonist of the formula (I):

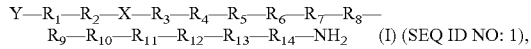
$R_9$—$R_{10}$—$R_{11}$—$R_{12}$—$R_{13}$—$R_{14}$—$NH_2$  (I) (SEQ ID NO: 1), wherein:
X is (4-Aminomethyl-biphenyl-3-yl)-acetic acid (Cba), (5-piperazin-1-yl-indole-1-yl)-acetic acid (Cip), 3-(4-oxo-6-piperazin-1-yl-4H-quinazolin-3-yl)-propionic acid (HomPqa), (6-[1,4]diazepan-1-yl-4-oxo-4H-quinazolin-3-yl)-acetic acid (Dqa), (6-Oxo-2-piperazin-1-yl-1,6-dihydro-purin-7-yl)-acetic acid (Pdp), (2-Piperazin-1-yl-purin-7-yl)-acetic acid (Ppa), (6-Amino-2-piperazin-1-yl-9H-purin-8-yl)-acetic acid (Appa), ((1R,4S)-6-2-Aza-bicyclo[2.2.1]hept-5-yl-4-oxo-4H-quinazolin)-acetic acid (Bqa), (1-Oxo-7-piperazin-1-yl-1H-isoquinolin-2-yl)-acetic acid (Pipa),
Y is H or an acyl moiety,
$R_1$ is Ile, Ala, (D)Ile, N-methyl Ile, Aib, 1-1Aic, 2-2Aic, Ach or Acp,
$R_2$ is Lys, Ala, (D)Lys, N-methyl lys, Nle or (Lys-Gly),
$R_3$ is Arg, Ala, (D)Arg, N-methyl Arg, Phe, 3,4,5-Trifluoro Phe or 2,3,4,5,6-Pentafluoro Phe,
$R_4$ is His, Ala, (D)His, N-methyl His, 4-MeOApc, 3-Pal or 4-Pal,
$R_5$ is Tyr, Ala, (D)Tyr, N-methyl Tyr, Trp, Tic, Bip, Dip, (1)Nal, (2)Nal, 3,4,5-TrifluoroPhe or 2,3,4,5,6-Pentafluoro Phe,
$R_6$ is Leu, Ala, (D)Leu or N-methyl Leu,
$R_7$ is Asn, Ala or (D)Asn,
$R_8$ is Leu or Trp,
$R_9$ is Val, Ala, (D)Val or N-methyl Val,
$R_{10}$ is Thr, Ala or N-methyl Thr,
$R_{11}$ is Arg, (D)Arg or N-methyl Arg,
$R_{12}$ is Gln or Ala,
$R_{13}$ is Arg, (D)Arg or N-methyl Arg, and
$R_{14}$ is Tyr, (D) Tyr or N-methyl Tyr, modified-Tyr, Phe, modified-Phe, (1) Nal, (2) Nal, Cha, C-alpha-methyl Tyr, or Trp, or a pharmaceutically acceptable salt thereof.

In another embodiment of the present invention, provided is a neuropeptide-2 receptor agonist having formula (II):

Y-Ile-Lys-X-Arg-His-Tyr-Leu-Asn-Trp-Val-Thr-Arg-Gln-(NMe)Arg-Tyr-$NH_2$  (II) (SEQ ID NO: 2)

wherein:
X is (4-Aminomethyl-biphenyl-3-yl)-acetic acid (Cba), (5-piperazin-1-yl-indole-1-yl)-acetic acid (Cip), 3-(4-oxo-6-piperazin-1-yl-4H-quinazolin-3-yl)-propionic acid (HomPqa), (6-[1,4]diazepan-1-yl-4-oxo-4H-quinazolin-3-yl)-acetic acid (Dqa), (6-Oxo-2-piperazin-1-yl-1,6-dihydro-purin-7-yl)-acetic acid (Pdp), (2-Piperazin-1-yl-purin-7-yl)-acetic acid (Ppa), (6-Amino-2-piperazin-1-yl-9H-purin-8-yl)-acetic acid (Appa), ((1R,4S)-6-2-Aza-bicyclo[2.2.1]hept-5-yl-4-oxo-4H-quinazolin)-acetic acid (Bqa), (1-Oxo-7-piperazin-1-yl-1H-isoquinolin-2-yl)-acetic acid (Pipa), and
Y is an acyl moiety,
or a pharmaceutically acceptable salt thereof.

In a further embodiment of the present invention, provided is a pharmaceutical composition, comprising a therapeutically effective amount of the neuropeptide-2 receptor agonist according to claim 1, or a salt thereof, and a pharmaceutically acceptable carrier.

The compounds of the invention are advantageous because, for example, they are truncated versions of the $PYY_{3-36}$. The shorter peptides, for example, not only facilitate easier synthesis and purification of the compounds, but also improve and reduce manufacturing procedures and expenses. Moreover, the compounds of the invention will interact preferably with Y2-receptors and not with homologous receptors such as NPY Y1, Y4 and Y5. Unwanted agonist or antagonist side reactions are, thereby, minimized.

It is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Although any methods, devices and materials similar or equivalent to those described herein can be used in the practice or testing of the invention, the preferred methods, devices and materials are now described.

All peptide sequences mentioned herein are written according to the usual convention whereby the N-terminal amino acid is on the left and the C-terminal amino acid is on the right, unless noted otherwise. A short line between two amino acid residues indicates a peptide bond. Where the amino acid has isomeric forms, it is the L form of the amino acid that is represented unless otherwise expressly indicated. For convenience in describing this invention, the conventional and nonconventional abbreviations for the various amino acids are used. These abbreviations are familiar to those skilled in the art, but for clarity are listed below:
Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine; Ile=I=Isoleucine; Leu=L=Leucine; Lys=K=Lysine; Met=M=Methionine; Phe=F=Phenylalanine; Pro=P=Proline; Ser=S=Serine; Thr=T=Threonine; Trp=W=Tryptophan; Tyr=Y=Tyrosine; Cys=C=Cysteine; and Val=V=Valine.

Also for convenience, the following abbreviations or symbols are used to represent the moieties, reagents and the like used in this invention:
Pqa is (4-oxo-6-piperazin-1-yl-4H-quinazolin-3-yl)-acetic acid;
Cba is (4-Aminomethyl-biphenyl-3-yl)-acetic acid;
Cip is (5-Piperazin-1-yl-indole-1-yl)-acetic acid;
HomPqa is 3-hydroxy-2-(4-oxo-6-piperazin-1-yl-4H-quinazolin-3-yl)-propionic acid,
Dqa is (6-[1,4]diazepan-1-yl-4-oxo-4H-quinazolin-3-yl)-acetic acid;
Pdp is (6-Oxo-2-piperazin-1-yl-1,6-dihydropurin-7-yl)-acetic acid;
Ppa is (2-Piperazin-1-yl-purin-7-yl)-acetic acid;
Appa is (6-Amino-2-piperazin-1-yl-9H-purin-8-yl)-acetic acid;
Bqa is ((1R,4S)-6-2-Aza-bicyclo[2.2.1]hept-5-yl-4-oxo-4H-quinazolin)-acetic acid;
Pipa is (1-Oxo-7-piperazin-1-yl-1H-isoquinolin-2-yl)-acetic acid;
Fmoc is 9-Fluorenylmethyloxycarbonyl;
Mtt is 4-Methyltrityl;
2Pip is 2-Phenylisopropyl ester;
Pmc is 2,2,5,7,8-Pentamethylchroman-6-sulfonyl;

$CH_2Cl_2$ is Methylene chloride;
$Ac_2O$ is Acetic anhydride;
$CH_3CN$ is Acetonitrile;
DMAc is Dimethylacetamide;
DMF is Dimethylformamide;
DIPEA is N,N-Diisopropylethylamine;
TFA is Trifluoroacetic acid;
$iPr_3SiH$ is Triisopropylsilane;
HOBT is N-Hydroxybenzotriazole;
DIC is N,N'-Diisopropylcarbodiimide;
BOP is Benzotriazol-1-yloxy-tris-(dimethylamino)phosphonium-Hexafluorophosphate;
HBTU is 2-(1H-Benzotriazole-1-yl)-1,1,3,3-tetramethyluronium-Hexafluorophosphate;
NMP is 1-methyl2-Pyrolidenone;
Tmob is 2,4,6-trimethoxybenzyl;
Dod is 4,4-Dimethoxydityl, (Bis-(4-methoxyphenyl)-methyl)
Trt is trityl;
Mts is mesitylene-2-sulfonyl;
FAB-MS is Fast atom bombardment ionization mass spectrometry; and
ES-MS is Electro spray ionization mass spectrometry.

As used herein, the term "acyl" means an optionally substituted alkyl, cycloalkyl, heterocyclic, aryl or heteroaryl group bound via a carbonyl group and includes groups such as acetyl, propionyl, benzoyl, 3-pyridinylcarbonyl, 2-morpholinocarbonyl, 4-hydroxybutanoyl, 4-fluorobenzoyl, 2-naphthoyl, 2-phenylacetyl, 2-methoxyacetyl and the like.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, bornyl, adamantyl, and the like. In a preferred embodiment, the "cycloalkyl" moieties can optionally be substituted with one, two, three or four substituents, with the understanding that said substituents are not, in turn, substituted further unless indicated otherwise. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further.

The term "lower alkyl", alone or in combination with other groups, refers to a branched or straight-chain alkyl radical of one to nine carbon atoms, preferably one to six carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, napthyl, 1,2,3,4-tetrahydronaphtalene, 1,2-dihydronaphtalene, indanyl, 1H-indenyl and the like.

The alkyl, loweralkyl and aryl groups may be substituted or unsubstituted. When substituted, there will generally be, for example, 1 to 4 substituents present, with the understanding that said substituents are not, in turn, substituted further unless indicated otherwise. These substituents may optionally form a ring with the alkyl, loweralkyl or aryl group they are connected with.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

The present representative compounds may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods. Such methods are disclosed in, for example, Merrifield, R. B., J. Amer. Chem. Soc. 85, 2149-2154 (1963); Barany et al., The Peptides, Analysis, Synthesis and Biology, Vol. 2, Gross, E. and Meienhofer, J., Eds. Academic Press 1-284 (1980), which are incorporated herein by reference.

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group on an amino acid or fragment while that entity reacts at the carboxyl group, followed by the selective removal of the alpha amino protecting group at allow a subsequent reaction to take place at that site. While specific protecting groups have been disclosed in regard to the solid phase synthesis method, it should be noted that each amino acid can be protected by a protective group conventionally used for the respective amino acid in solution phase synthesis.

Alpha amino groups may be protected by a suitable protecting group selected from aromatic urethane-type protecting groups, such as allyloxycarbonyl, benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenylmethyloxycarbonyl (Fmoc) and p-methoxybenzyloxycarbonyl (Moz); aliphatic urethane-type protecting groups, such as t-butyloxycarbonyl (Boc), diisopropylmethyloxycarbonyl, and isopropyloxycarbonyl. Herein, Fmoc is most preferred for alpha amino protection.

Guanidino groups may be protected by a suitable protecting group such as nitro, p-toluenesulfonyl (Tos), (Z,) pentamethylchromanesulfonyl (Pmc), 4-Methoxy-2,3,6,-trimethylbenzenesulfonyl (Mtr), (Pmc), and (Mtr) are most preferred for arginine (Arg).

The epsilon-amino groups may be protected by a suitable protecting group such as 2-chloro benzyloxycarbonyl (2-Cl—Z), 2-Bromo benztloxycarbonyl (2-Br—Z)- and t-butyloxycarbonyl (Boc). Boc is the most preferred for (Lys).

Hydroxyl groups (OH) may be protected by a suitable protecting group such as benzyl (Bzl), 2,6-dichlorobenzyl (2,6-diCl-Bzl), and tert.-Butyl (t-Bu). (t-Bu) is most preferred for (Tyr), (Ser) and (Thr).

The beta- and gamma-amide groups of Asn and Gln may be protected by a suitable protecting group such as 4-methyltrityl (Mtt), 2,4,6-trimethoxybenzyl (Tmob), 4,4-Dimethoxydityl Bis-(4-methoxyphenyl)-methyl (Dod) and Trityl (Trt). Trt is the most preferred for (Asn) and (Gln).

The indole group may be protected by a suitable protecting group selected from formyl (For), Mesityl-2-sulfonyl (Mts) and t-butyloxycarbonyl (Boc). Boc is the most preferred for (Trp).

The imidazol group may be protected by a suitable protecting group selected from Benzyl (Bzl), t-butyloxycarbonyl (Boc), and Trityl (Trt). Trt is the most preferred for (His).

The synthesis of the amino acid Pqa is described by J. Hutchinson et. al (J. Med. Chem. 1996, 39, 4583-4591). The Fmoc-Pqa derivative was purchased from NeoMPS, Inc. (San Diego Calif.)

{4'-[(9H-fluoren-9-ylmethoxycarbonylamino)-methyl]-biphenyl-3-yl}-acetic acid (Fmoc-Cba-OH) may be prepared by conventional means, for example by carrying out a Suzuki coupling between a 4-bromophenylacetic acid methyl ester and a 4-formylphenyl boronic acid followed by reductive amination of the resulting 4'-formylbiphenylacetic acid methyl ester to give an aminomethylbiphenylacetic acid derivative. An example of a typical Suzuki coupling is provided in H. Heitsch, et al, Synthesis 1996, 1325. Reductive amination can be carried out via standard methods as reviewed in E. Baxter, et al. Organic Reactions 2002, 59, 1-714. Ester hydrolysis and protection of the amino group as a 9H-fluoren-9-ylmethoxycarbonyl derivative are standard transformation. Typical procedures are described in the description of the preparation of intermediates.

All solvents, isopropanol (iPrOH), methylene chloride ($CH_2Cl_2$), dimethylformamide (DMF) and N-methylpyrrolinone (NMP) were purchased from Fisher or Burdick & Jackson and were used without additional treatment. Trifluoroacetic acid was purchased from Halocarbon or Fluka and used without further purification.

Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, or Neosystem. Purity of these reagents was confirmed by thin layer chromatography, NMR and melting point prior to use. Benzhydrylamine resin (BHA) was a copolymer of styrene—1% divinylbenzene (100-200 or 200-400 mesh) obtained from Bachem or Advanced Chemtech. Total nitrogen content of these resins were generally between 0.3-1.2 meq/g.

In a preferred embodiment, peptides were prepared using solid phase synthesis by the method generally described by Merrifield, (J. Amer. Chem. Soc., 85, 2149 (1963)), although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-((R,S)-α-(1-(9H-fluoren-9-yl)-methoxyformamido)-2,4-dimethyloxybenzyl)-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

Typically, the amino acids or mimetic are coupled onto the Fmoc-Linker-BHA resin using the Fmoc protected form of amino acid or mimetic, with 2-5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The alpha amino Fmoc protecting groups are removed under basic conditions. Piperidine, piperazine or morpholine (20-40% v/v) in DMF may be used for this purpose. Preferably 40% piperidine in DMF is utilized.

Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yl-oxy-tri-(dimethylamino)phosphonium hexafluorophosphate (BOP), Bromo-tris-pyrrolidino-phosphonium hexafluorophosphate (PyBroP), 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents are described by Barany and Merrifield (in The Peptides, Vol. 2, J. Meienhofer, ed., Academic Press, 1979, pp 1-284) and may be utilized. Various reagents such as 1-hydroxybenzotriazole (HOBT), N-hydroxysuccinimide (HOSu) and 3,4-dihydro-3-hydroxy-4-oxo-1,2,3-benzotriazine (HOBT) may be added to the coupling mixtures in order to optimize the synthetic cycles. Preferred here is HOBT.

For preparation of N-terminal acetyl derivatives, acetylation was carried out by treating the resin bound peptide with 20% acetic anhydride in DMF with 5% DIEA. For other N-terminal acylations, acylation was carried out using the corresponding carboxylic acid activated in-situ with DIC/HOBt for 30 minutes.

The protocol for a typical synthetic cycle is as follows:

| Protocol 1 | | |
|---|---|---|
| Step | Reagent | Time |
| 1 | DMF | 2 × 30 sec. |
| 2 | 20% piperidine/DMF | 1 min. |
| 3 | 20% piperidine/DMF | 15 min. |
| 4 | DMF | 2 × 30 sec. |
| 5 | iPrOH | 2 × 30 sec. |
| 6 | DMF | 3 × 30 sec. |
| 7 | Coupling | 60 min-18 hours. |
| 8 | DMF | 2 × 30 sec. |
| 9 | iPrOH | 1 × 30 sec. |
| 10 | DMF | 1 × 30 sec. |
| 11 | $CH_2Cl_2$ | 2 × 30 sec. |

Solvents for all washings and couplings were measured to volumes of 10-20 ml/g resin. Coupling reactions throughout the synthesis were monitored by the Kaiser Ninhydrin test to determine extent of completion (Kaiser et at. Anal. Biochem. 34, 595-598 (1970)). Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For most compounds, the blocking groups were removed and the peptide cleaved from the resin. For example, the peptide-resins were treated with 100 μL ethanedithiol, 100 μl dimethylsulfide, 300 μL anisole, and 9.5 mL trifluoroacetic acid, per gram of resin, at room temperature for 180 min. Or alternately the peptide-resins were treated with 1.0 mL triisopropyl silane and 9.5 mL trifluoroacetic acid, per gram of resin, at room temperature for 180 min. The resin was filtered off and the filtrates were precipitated in chilled ethyl ether. The precipitates were centrifuged and the ether layer was decanted. The residue was washed with two or three volumes of $Et_2O$ and recentrifuged. The crude products were dried under vacuum.

Purification of the crude peptides was preferably performed on Shimadzu LC-8A system by high performance liquid chromatography (HPLC) on a reverse phase C-18 Column (50×250 mm. 300 Å, 10-15 μm). The peptides were injected to the columns in a minimum volume of either 0.1 $AcOH/H_2O$ or $CH_3CH/H_2O$. Gradient elution was generally started at 2% B buffer, 2%-70% B over 70 minutes, (buffer A: 0.1% $TFA/H_2O$, buffer B: 0.1% $TFA/CH_3CN$) at a flow rate of 50 ml/min. UV detection was made at 220/280 nm. The fractions containing the products were separated and their purity was judged on Shimadzu LC-10AT analytical system using reverse phase Ace C18 column (4.6×50 mm) at a flow rate of 2 ml/min., gradient (2-70%) over 10 min. (buffer A: 0.1% $TFA/H_2O$, buffer B: 0.1% $TFA/CH_3CN$)). Fractions judged to be of high purity were pooled and lyophilized.

Purity of the final products was checked by analytical HPLC on a reversed phase column as stated above. Purity of all products was judged to be approximately 95-99%. All final products were also subjected to fast atom bombardment mass spectrometry (FAB-MS) or electrospray mass spectrometry (ES-MS). All products yielded the expected parent M+H ions within acceptable limits.

The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. Any procedure for obtaining a pharmaceutically acceptable salt known to a skilled artisan can be used.

In the practice of the method of the present invention, an effective amount of any one of the peptides of this invention or a combination of any of the peptides of this invention or a pharmaceutically acceptable salt thereof, is administered via any of the usual and acceptable methods known in the art, either singly or in combination. Administration can be, for example, once a day, once every three days or once a week. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose for intranasal administration is typically in the range of about 0.001 to about 0.1 mg/kg body weight. In humans, the preferred subcutaneous dose based on peptide content is from about 0.001 mg to about 100 mg; preferably from about 0.1 mg to about 15 mg.

Preparation of Intermediates

Preparation of intermediate 1. The intermediate utilized in example 6 (4-(1-carboxymethyl-1H-indol-5-yl)-piperazine-1-carboxylic acid 9H-fluoren-9-ylmethyl ester (Fmoc-Cip-OH) was prepared as follows.

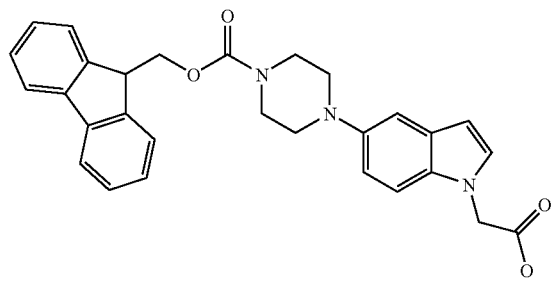

Step 1: Preparation of
1-(3-methyl-4-nitro-phenyl)-piperazine

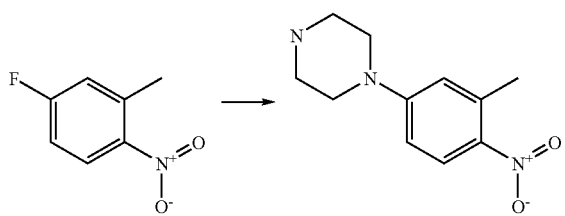

Piperazine (86.14 g) and dimethylforamide (150 mL) were stirred at 110° C. to effect solution. At this time, a solution of 4-fluoro-2-methyl-1-nitro-benzene (100 mL) dissolved in 10 mL of dimethylforamide was added over 3 minutes and then stirred at 100° C. for 30 min. At this time, crushed ice and water (700 mL) were added to the reaction mixture and the resulting yellow solid was filtered off. The filtrate was washed with 300 mL of water and then dried in a vacuum oven. In this way, 19.40 g of solid was obtained. $H^1$-NMR spectroscopy indicated a spectrum consistent with 1-(3-methyl-4-nitro-phenyl)-piperazine.

Step 2: Preparation of 4-(3-methyl-4-nitro-phenyl)-piperazine-1-carboxylic acid tert-butyl ester

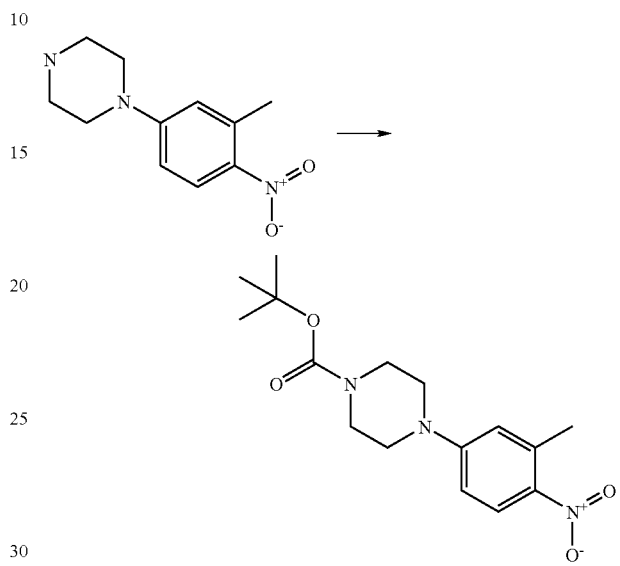

1-(3-methyl-4-nitro-phenyl)-piperazine (19.40 g) and 4-dimethylaminopyridine (0.20 gram) were stirred to effect solution in 200 mL of tetrahydrofuran at room temperature. Then 96.45 g of carbonic acid di-tert-butyl ester (Boc)$_2$O was added in one portion. This mixture was stirred at room temperature for 1 hour. At this time, the reaction mixture was evaporated to dryness, resulting in a yellow solid which was suspended in 400 mL of water for 15 minutes before filtration and washing of the solid with water. The solid remaining after filtration was dried in vacuo leaving 27.9 g. $H^1$-NMR spectroscopy indicated a spectrum consistent with 4-(3-methyl-4-nitro-phenyl)-piperazine-1-carboxylic acid tert-butyl ester.

Step 3: Preparation of 4-[4-nitro-3-((E)-2-pyrrolidin-1-yl-vinyl)-phenyl]-piperazine-1-carboxylic acid tert-butyl ester

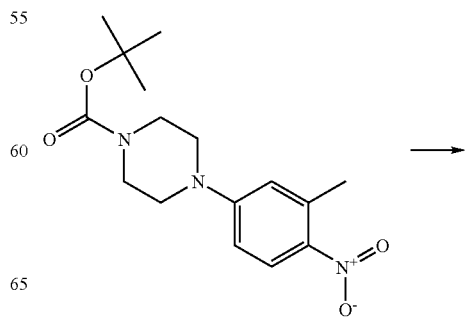

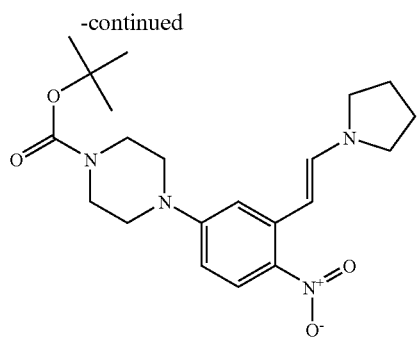

4-(3-Methyl-4-nitro-phenyl)-piperazine-1-carboxylic acid tert-butyl ester (27.9 g) was dissolved in 50 mL of DMF; to this solution was added N,N-dimethylformamide dimethylacetal (DMF-DMA) and the mixture was then heated to 100° C. for 18 hours. At this time, the mixture was diluted with water and the aqueous layer was extracted with ethyl acetate. The organic layer was washed four times with water, dried over magnesium sulfate and filtered. The filtrate was concentrated under vacuum, leaving a red oil. This oil was triturated with a mixture of diethyl ether and hexane to give 31.31 g of the expected product. $H^1$-NMR spectroscopy indicated a spectrum consistent with 4-[4-nitro-3-((E)-2-pyrrolidin-1-yl-vinyl)-phenyl]-piperazine-1-carboxylic acid tert-butyl ester.

Step 4: Preparation of 4-(1H-indol-5-yl)-piperazine-1-carboxylic acid tert-butyl ester

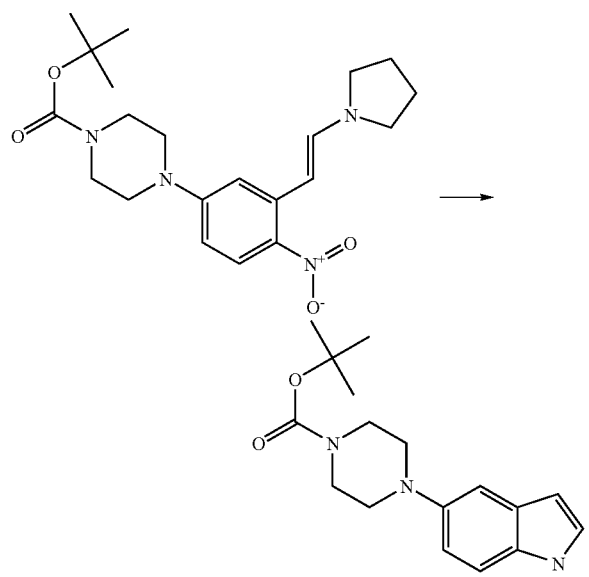

4-[4-Nitro-3-((E)-2-pyrrolidin-1-yl-vinyl)-phenyl]-piperazine-1-carboxylic acid tert-butyl ester was stirred in 50 mL of methanol under a nitrogen atmosphere at room temperature. To this mixture was added 1.5 mL of Raney nickel followed by 2.35 g of hydrazine. This mixture was stirred for 15 minutes. At this time, another 1.17 g of hydrazine was added and the mixture was stirred overnight. Next, the reaction mixture was filtered through celite and the filtrate was concentrated in vacuo. The residue was portioned into a mixture of diethyl ether and water. The organic layer was separated, dried with magnesium sulfate, diluted with an equal volume of hexane and filtered through a silica gel plug eluting with 1:1 (vol/vol) diethyl ether/hexane. Concentration of the filtrate in vacuo provided a solid which was triturated with a mixture of diethyl ether/hexane. This resulted in 3.33 g of an off-white solid. $H^1$-NMR spectroscopy indicated a spectrum consistent with 4-(1H-indol-5-yl)-piperazine-1-carboxylic acid tert-butyl ester.

Step 5: Preparation of 4-(1-tert-butoxycarbonylmethyl-1H-indol-5-yl)-piperazine-1-carboxylic acid tert-butyl ester

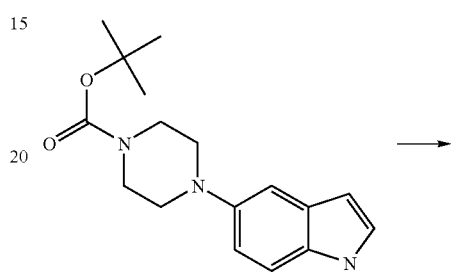

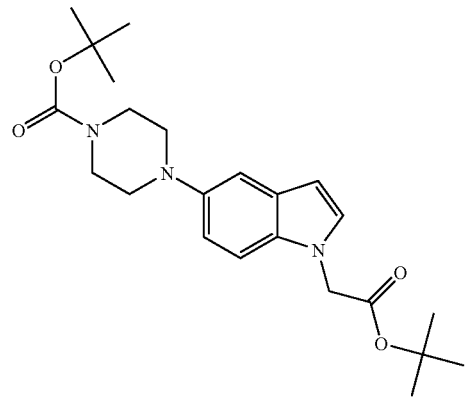

4-(1H-Indol-5-yl)-piperazine-1-carboxylic acid tert-butyl ester (8.50 g) was stirred in 70 mL of DMF and cooled with an ice/water bath. To this mixture sodium hydride (1.35 g of 60% dispersion in mineral oil) was added in portions. After addition was completed, the mixture was stirred for 30 minutes at 0° C. before the addition of 7.15 g of bromo-acetic acid tert-butyl ester. The reaction mixture was allowed to reach room temperature while stirring for 2 hours. At this time, brine was added to the mixture; ethyl acetate was used for extraction of the organic soluble components. The organic layer was washed with water four times, then dried with magnesium sulfate and filtered. The filtrate was concentrated in vacuo leaving a reddish oil which was dissolved in 70 mL of hexane. Upon standing for 3 days, a precipitate formed. After filtration and washing of the precipitate with pentane, the solid was dried. In this manner, 8.85 g of the desired product was obtained. $H^1$-NMR spectroscopy indicated a spectrum consistent with 4-(1-tert-butoxycarbonylmethyl-1H-indol-5-yl)-piperazine-1-carboxylic acid tert-butyl ester.

Step 6: Preparation of (5-piperazin-1-yl-indol-1-yl)-acetic acid

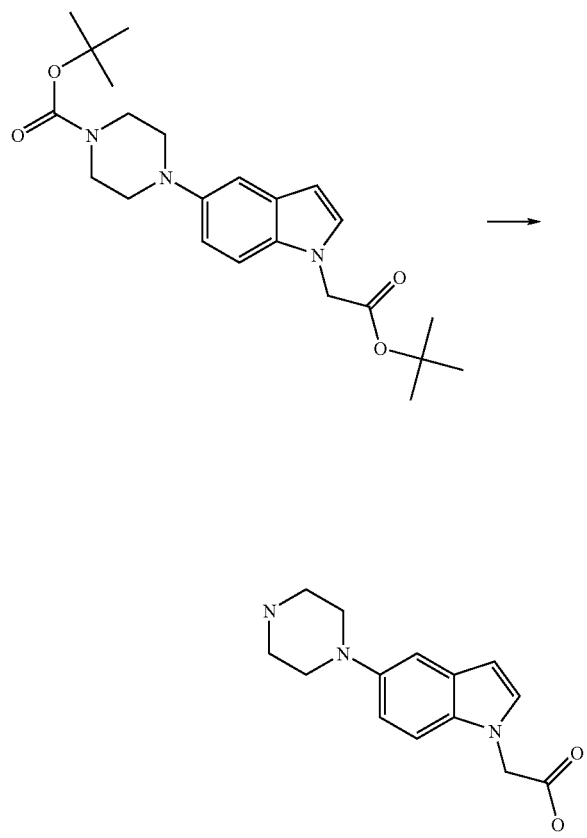

4-(1-tert-butoxycarbonylmethyl-1H-indol-5-yl)-piperazine-1-carboxylic acid tert-butyl ester (8.80 g) was treated with a mixture of 60 mL of TFA in 120 mL of methylene chloride overnight at room temperature. At this time, the solvent was removed in vacuo. This resulted in 11.26 g of a light yellow residue. This residue was used without further purification in the next step.

Step 6: Preparation of 4-(1-carboxymethyl-1H-indol-5-yl)-piperazine-1-carboxylic acid 9H-fluoren-9-ylmethyl ester

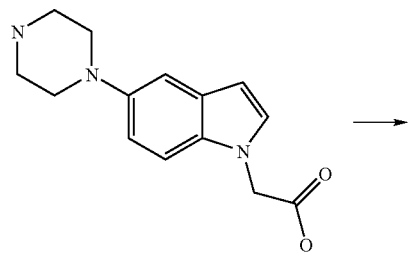

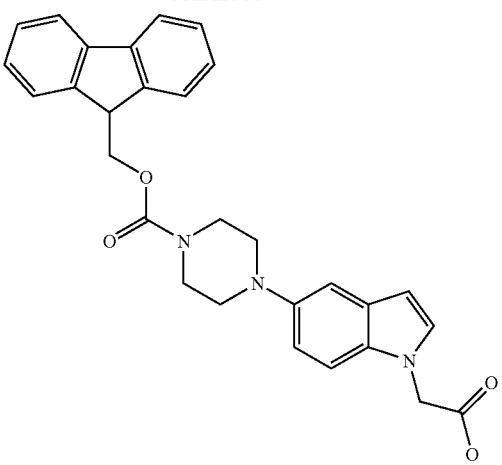

To a portion of the residue obtained in the last step was added 6.65 g of potassium carbonate and 20 mL each of dioxane and water. To this mixture was added in portions chloroformic acid 9-fluorenylmethyl ester (2.49 g). This mixture was then stirred for 1 hour and then diluted with water. Acetic acid was used to acidify the reaction mixture. The mixture was then extracted with ethyl acetate and the organic layer was concentrated in vacuo. The residue remaining from ethyl acetate removal was filtered through a silica gel column chromatography eluting with ethyl acetate, followed by 10% methanol in methylene chloride (vol/vol). The combined fractions were then treated with 300 mL of water containing 5 g of potassium carbonate and this mixture was extracted twice with diethyl ether. The ether layer was discarded and the aqueous layer was acidified with acetic acid. This resulted in the formation of a white solid that was collected by filtration. The solid was washed with water and dried in a vacuum oven over phosphorous pentaoxide. In this manner, 1.71 g of a product was obtained. $H^1$-NMR mass spectroscopic techniques indicated a spectra consistent with 4-(1-carboxymethyl-1H-indol-5-yl)-piperazine-1-carboxylic acid 9H-fluoren-9-ylmethyl ester.

Preparation of intermediate 2. The intermediate utilized in example 7 4-[3-(1-carboxy-2-hydroxy-ethyl)-4-oxo-3,4-dihydro-quinazolin-6-yl]-piperazine-1-carboxylic acid 9H-fluoren-9-ylmethyl ester (Fmoc-HmoPqa-OH) was prepared as follows.

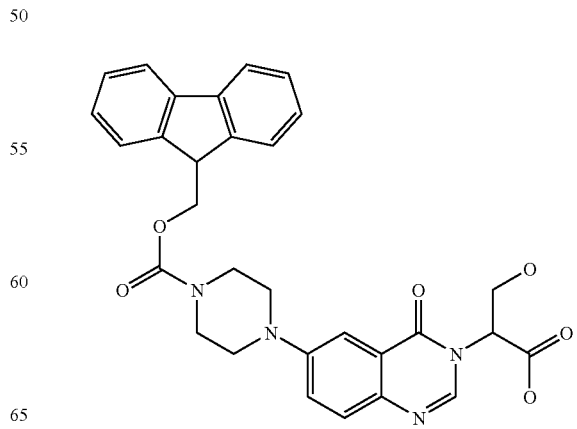

Step 1: Preparation of 2-nitro-5-piperazin-1-yl-benzoic acid

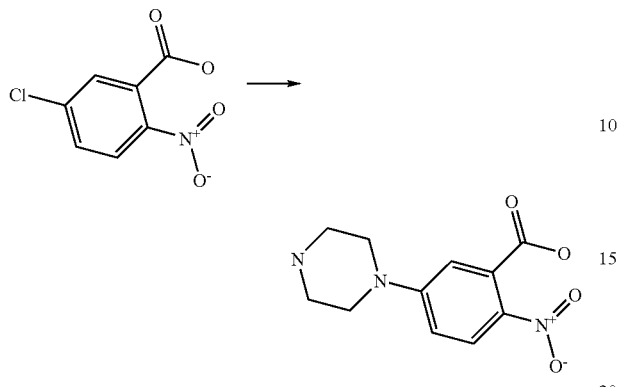

5-Chloro-2-nitro-benzoic acid (44 g) and piperizine (90 g, 4.8 eq.) were mixed without solvent and heated at 110° C. for 6 hours and then stirred at room temperature over night. At this time, the mixture had solidified. To this solid was added 10% KHSO$_4$ (wt/vol, pH 4 to 5) aqueous solution and the mixture was sonicated. The supernatant was decanted and fresh 10% KHSO$_4$ (wt/vol) aqueous solution was added. A total of 1.8 liters of 10% KHSO4 (wt/vol) aqueous solution was added and decanted in this manner. After stirring at room temperature, the solid was filtered and rinsed with water. The remaining solid was dried in a vacuum oven, leaving a yellow-orange solid (53.1 g). This material was carried forward to the next step without further purification.

Step 2: Preparation of 4-(3-carboxy-4-nitro-phenyl)-piperazine-1-carboxylic acid 9H-fluoren-9-ylmethyl ester

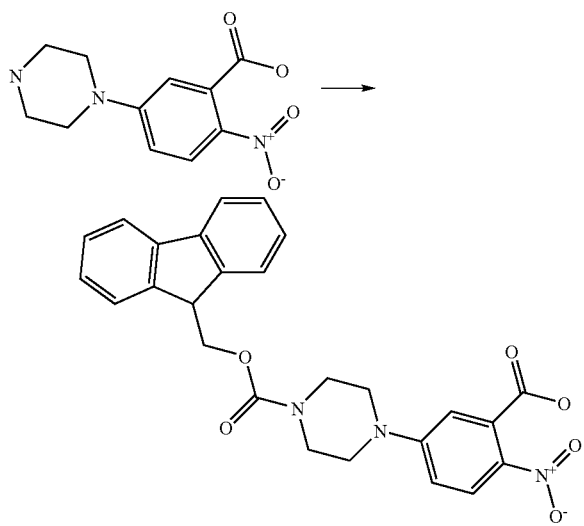

The solid from the previous reaction (15 g) was suspended in 10% NaHCO$_3$ (wt/vol) aqueous solution (150 mL) and dioxane (120 mL). The reaction mixture was cooled to 0° C. and to this suspension was added during the course of 40 minutes a solution of chloroformic acid 9-fluorenylmethyl ester (14.74 g) in dioxane (70 mL). The reaction mixture was allowed to reach room temperature and was stirred overnight. At this time, water and ethyl acetate were added to the reaction mixture and the phases were separated. The aqueous phase was separated and then acidified with concentrated hydrochloric acid to pH 3 to 4. The precipitated solid was filtered and washed with water, followed by drying in a vacuum oven. In this manner was obtained 17.86 g of solid. H$^1$-NMR spectroscopy indicated a spectrum consistent with 4-(3-carboxy-4-nitro-phenyl)-piperazine-1-carboxylic acid 9H-fluoren-9-ylmethyl ester.

Step 3: Preparation of 4-[3-(2-tert-butoxy-1-tert-butoxycarbonyl-ethylcarbamoyl)-4-nitro-phenyl]-piperazine-1-carboxylic acid 9H-fluoren-9-ylmethyl ester

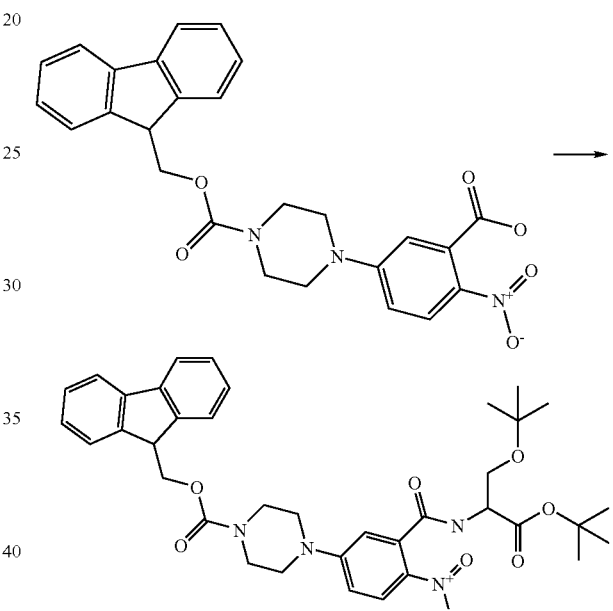

To a suspension of 4-(3-carboxy-4-nitro-phenyl)-piperazine-1-carboxylic acid 9H-fluoren-9-ylmethyl ester (16.8 g) and O-tert-butyl-L-serine tert-butyl ester hydrochloride (9.0 g) in methylene chloride was added 35.5 mmol of N-hydroxybenzotriazole and the reaction mixture was cooled to 0° C. To this suspension was added triethylamine (10.4 mL). This caused the suspension to become a solution. At this point, 1-ethyl-3-(3-dimethyllaminopropyl)carbodiimide hydrochloride (7.5 g) was added. The reaction mixture was stirred at 0° C. for 1 hour and then at room temperature for 2 days. At this time, the methylene chloride was removed in vacuo and ethyl acetate was added, resulting in formation of a solid. The ethyl acetate was evaporated and methylene chloride was added. This organic layer was washed with 10% KHSO$_4$ (wt/vol) aqueous solution and with brine, followed by washing with 5% NaHCO$_3$ (wt/vol) aqueous solution and finally with brine again. The organic layer was dried with magnesium sulfate, filtered and evaporated to dryness to give a solid. This solid was triturated with hot ethyl acetate (~2 L). This dissolved most of the solid. The resulting solution was again dried with magnesium sulfate, filtered and evaporated to dryness, providing an orange oil which solidified upon cooling to room temperature. This solid was triturated with diethyl ether at room temperature with stirring. Upon filtration and washing with pentane, 20 g of a solid was obtained. H¹-NMR spectroscopy indicated a spectrum consistent with 4-(3-carboxy-4-nitro-phenyl)-piperazine-1-carboxylic acid 9H-fluoren-9-yl-methyl ester.

Step 4: Preparation of 3-tert-butoxy-2-(2-nitro-5-piperazin-1-yl-benzoylamino)-propionic acid tert-butyl ester

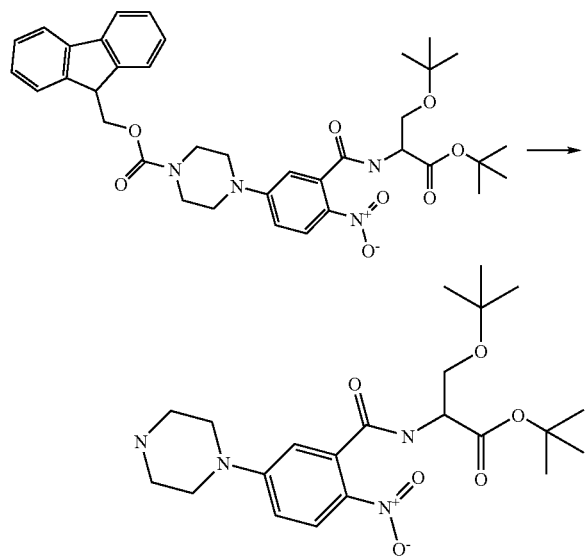

Dimethylfomamide (180 mL) was used to dissolve 4-(3-carboxy-4-nitro-phenyl)-piperazine-1-carboxylic acid 9H-fluoren-9-ylmethyl ester (17 g) and to this solution was added diethylamine (18 mL). This mixture was stirred at room temperature for 15 minutes. At this time, water and ethyl acetate were added. The organic phase was separated and dried with magnesium sulfate, filtered and concentrated in vacuo. The residue was triturated with diethyl ether at room temperature and the solid was filtered and washed with pentane. This resulted in 7.29 g of a solid. H¹-NMR spectroscopy indicated a spectrum consistent with 3-tert-butoxy-2-(2-nitro-5-piperazin-1-yl-benzoylamino)-propionic acid tert-butyl ester.

Step 5: Preparation of 4-[3-(2-tert-butoxy-1-tert-butoxycarbonyl-ethylcarbamoyl)-4-nitro-phenyl]-piperazine-1-carboxylic acid tert-butyl ester

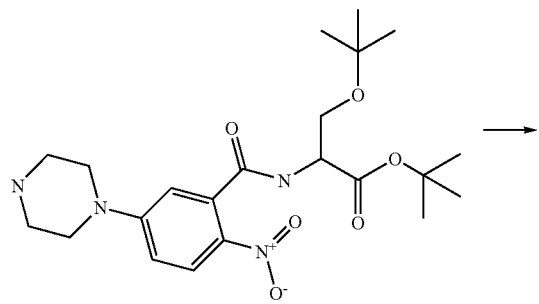

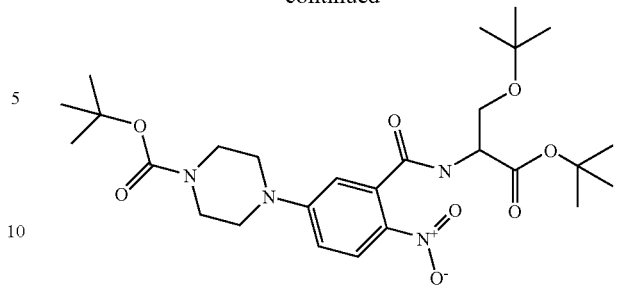

3-tert-Butoxy-2-(2-nitro-5-piperazin-1-yl-benzoylamino)-propionic acid tert-butyl ester (8.59 g) was dissolved in tetrahydrofuran (150 mL) and di-tert-butyl-dicarbonate (4.56 g) and 4-dimethylaminopyridine (230 mg) was added at room temperature. The reaction mixture was stirred at room temperature for 2 hours. At this time, the solvent was removed in vacuo and the residue was taken up in water and ethyl acetate. The combined organic phases were washed with 10% KHSO₄ (wt/vol) aqueous solution, with water, followed by washing with 5% NaHCO₃ (wt/vol) aqueous solution and finally with brine. The organic layer was dried with magnesium sulfate, filtered and evaporated to small volume. Upon addition of pentane, a solid precipitate was formed. The solid was filtered and dried in a vacuum oven. In this manner, 9.6 g of a solid were obtained. H¹-NMR spectroscopy indicated a spectrum consistent with 4-[3-(2-tert-butoxy-1-tert-butoxycarbonyl-ethylcarbamoyl)-4-nitro-phenyl]-piperazine-1-carboxylic acid tert-butyl ester.

Step 6: Preparation of 4-[4-amino-3-(2-tert-butoxy-1-tert-butoxycarbonyl-ethylcarbamoyl)-phenyl]-piperazine-1-carboxylic acid tert-butyl ester

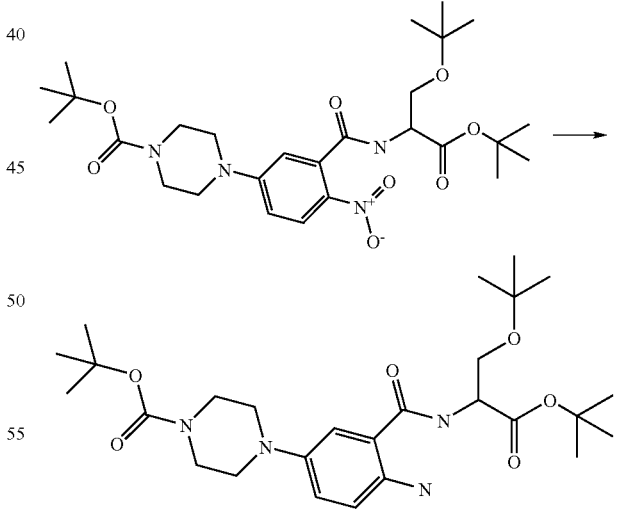

4-[3-(2-tert-Butoxy-1-tert-butoxycarbonyl-ethylcarbamoyl)-4-nitro-phenyl]-piperazine-1-carboxylic acid tert-butyl ester (10 g) was dissolved in 250 mL of methanol. This solution was treated with 1.2 g of 10% (wt/wt) palladium on carbon catalyst under nitrogen atmosphere. The mixture was then degassed before stirring under 1 atmosphere of hydrogen gas at room temperature for approximately 2.5 hours. At this time, the reaction mixture was filtered through celite and washed with copious volumes of methanol. The dark filtrate was concentrated in vacuo and the residue was further dried over phosphorous pentaoxide. In this manner, 9.49 g of the expected product was obtained as a grey-purple solid. H[1]-NMR spectroscopy indicated a spectrum consistent with 4-[4-amino-3-(2-tert-butoxy-1-tert-butoxycarbonyl-ethyl-carbamoyl)-phenyl]-piperazine-1-carboxylic acid tert-butyl ester.

Step 7: Preparation of 4-[3-(2-tert-butoxy-1-tert-butoxycarbonyl-ethyl)-4-oxo-3,4-dihydro-quinazolin-6-yl]-piperazine-1-carboxylic acid tert-butyl ester

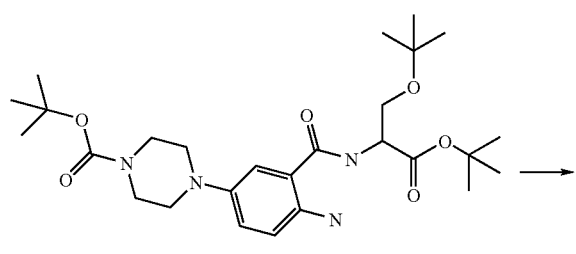

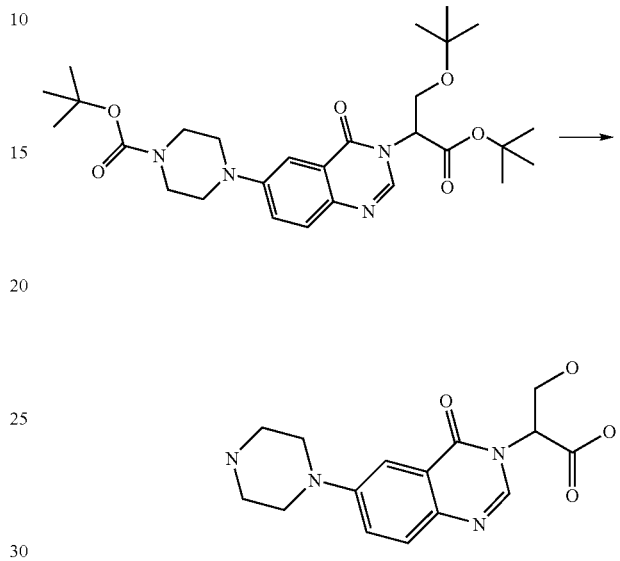

4-[4-amino-3-(2-tert-butoxy-1-tert-butoxycarbonyl-ethyl-carbamoyl)-phenyl]-piperazine-1-carboxylic acid tert-butyl ester (8.7 g) was dissolved in 4.63 g of formamidine acetate and this mixture was heated to 100 to 115° C. for 40 minutes. At that time, the reaction mixture was cooled to room temperature and the mixture was concentrated in vacuo. The residue was taken up in ethyl acetate and water. The organic phase was separated and washed with brine, followed by drying with magnesium sulfate. Upon filtration and concentration of the filtrate in vacuo, a purple residue was obtained. This residue was purified by flash column chromatography (200 g of silica) eluted with a step gradient of ethyl acetate: hexane (20%, 30%, 35%). After the collections of appropriate fractions and removal of solvent in vacuo, the resulting residue was treated with pentane and evaporated again. After drying the residue in a vacuum oven, 5.7 g of a light foam were obtained. H[1]-NMR spectroscopy indicated a spectrum consistent with 4-[3-(2-tert-butoxy-1-tert-butoxycarbonyl-ethyl)-4-oxo-3,4-dihydro-quinazolin-6-yl]-piperazine-1-carboxylic acid tert-butyl ester.

Step 8: Preparation of 3-hydroxy-2-(4-oxo-6-piperazin-1-yl-4H-quinazolin-3-yl)-propionic acid 4-[3-(2-tert-butoxy-1-tert-butoxycarbonyl-ethyl)-4-oxo-3,4-dihydro-quinazolin-6-yl]-piperazine-1-carboxylic acid tert-butyl ester (4.7 g) was dissolved in anisole (8 mL) and cooled in an ice-water bath. Trifluoroacetic acid (80 mL) is added slowly. The mixture was stirred for 5 minutes while cooling with the ice-water bath and then for 5 hours at room temperature; during this time, the color of the reaction mixture changed from orange to red to purple to dark blue over time. At this time, the reaction solvents were removed in vacuo, leaving a blue oil. This oil was triturated with dry diethyl ether and evaporated to dryness again. The residue was again triturated with dry diethyl ether and stirred overnight with this solvent. At this time, the mixture was filtered and the resulting solid was washed with diethyl ether and dried in a vacuum oven, resulting in 4.4 g of a solid. This solid was used in the next step without further purification. H[1]-NMR spectroscopy indicated a spectrum consistent with 3-hydroxy-2-(4-oxo-6-piperazin-1-yl-4H-quinazolin-3-yl)-propionic acid.

Step 9: Preparation of 4-[3-(1-carboxy-2-hydroxy-ethyl)-4-oxo-3,4-dihydro-quinazolin-6-yl]-piperazine-1-carboxylic acid 9H-fluoren-9-ylmethyl ester

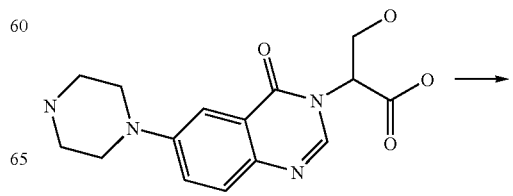

-continued

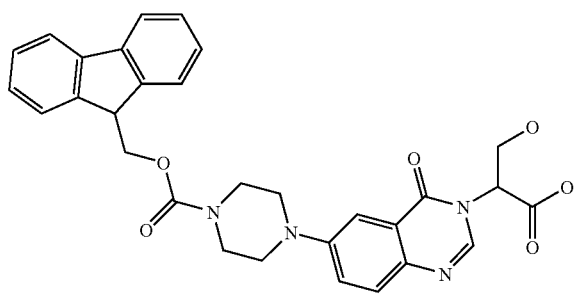

3-Hydroxy-2-(4-oxo-6-piperazin-1-yl-4H-quinazolin-3-yl)-propionic acid (8.85 mmol) was dissolved in 10% (wt/vol) aqueous sodium bicarbonate and was cooled in an ice bath. A solution of 2.96 g of carbonic acid 2,5-dioxo-pyrrolidin-1-yl ester 9H-fluoren-9-ylmethyl ester dissolved in 30 mL of dioxane was added drop-wise during 0.5 hour. The mixture was then stirred at 0° C. for 1 h and then at room temperature for 4 hours. Thin layer chromatography indicated the reaction was complete at 4 hours but stirring was continued overnight. At this time, the reaction mixture was diluted with water and extracted twice with ethyl acetate. The aqueous phase was cooled to 0° C. and acidified to pH 3 with 2 N HCl aq. The acidified aqueous phase was extracted thrice with ethyl acetate. The combined organic phases were washed with brine and dried with magnesium sulfate. After filtration, the filtrate was concentrated in vacuo until a solid began to precipitate. In this manner, 2.4 g of a solid was obtained. Further concentration of the filtrate resulted in a second precipitate (0.96 g). By addition of diethyl ether to the filtrate, a third fraction was obtained (1.15 g). The combined material amounted to 4.53 g. $H^1$-NMR spectroscopy indicated a spectrum consistent with 4-[3-(1-carboxy-2-hydroxy-ethyl)-4-oxo-3,4-dihydro-quinazolin-6-yl]-piperazine-1-carboxylic acid 9H-fluoren-9-ylmethyl ester.

Preparation of intermediate 3. The intermediate utilized in example 8, 4-(3-carboxymethyl-4-oxo-3,4-dihydro-quinazolin-6-yl)-[1,4]diazepane-1-carboxylic acid 9H-fluoren-9-ylmethyl ester, Fmoc-Dqa-OH) was prepared as follows.

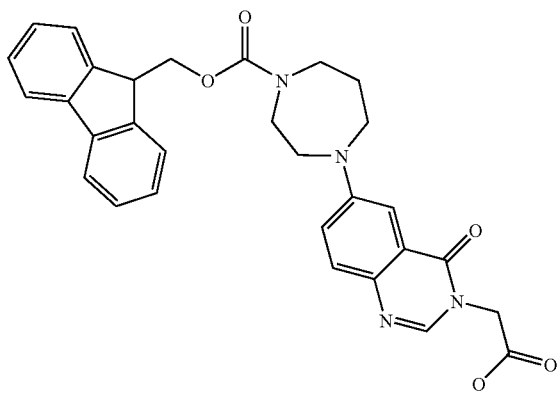

Step 1: Preparation of
5-[1,4]diazepan-1-yl-2-nitro-benzoic acid

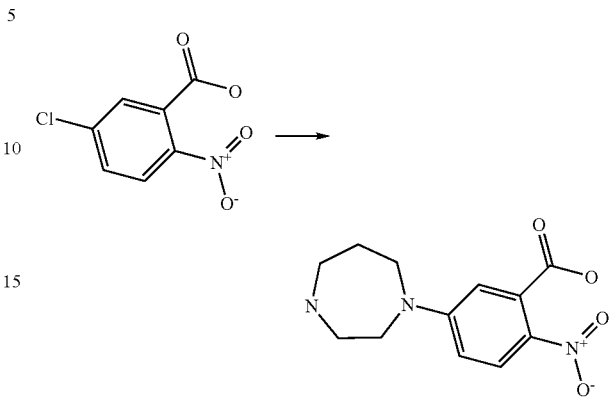

5-Chloro-2-nitro-benzoic acid (42.3 g) and homopiperizine (100 g, 4.8 eq.) were mixed without solvent and heated at 110° C. After 10 min, the mixture had melted into an orange, thick solution. After 45 min total reaction time, the mixture turned to a dark black-brown color and become very thick. At this time, the mixture was cooled to room temperature and diluted with 10% $KHSO_4$ (wt/vol) aqueous solution (pH 4). This mixture was stirred at room temperature for ~1 hour and then filtered. The solid was rinsed with a mixture of hexanes and diethyl ether, diethyl ether and then hexane. The solid was then dried under vacuum. This resulted in 40.8 g (73%) of a dark brown solid. The compound was carried on to the next step without further analysis or purification.

Step 2: Preparation of 4-(3-carboxy-4-nitro-phenyl)-[1,4]-diazepane-1-carboxylic acid tert-butyl ester

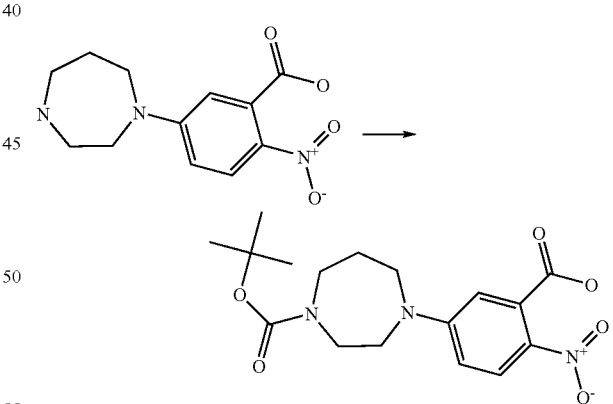

5-[1,4]Diazepan-1-yl-2-nitro-benzoic acid (40.8 g) was dissolved in 693 mL 1 N NaOH solution resulting in a dark brown solution. To this solution was added 1000 mL of dioxane. This mixture was cooled to 0° C. for 1 hour before the addition of $(Boc)_2O$ (53.8 g, 1.6 eq.). The reaction mixture was allowed to come to room temperature overnight with stirring. At this time, the solvent was removed in vacuo. The residue was then taken up in 2 L of water. The undissolved solid was filtered off. The aqueous filtrate was acidified with 10% aqueous $KHSO_4$ solution to pH 3. The precipitated solid was filtered off and rinsed with water. While still wet, the solid was triturated with ethyl acetate (~3 L). The above ethyl acetate filtrate was washed with 10% KHSO₄ and brine, followed by drying over magnesium sulfate. Upon filtration and concentration, a precipitate began to form. This precipitate was filtered and rinsed with diethyl ether and pentane. In this manner, 246 g (46%) of a light brown solid was obtained.

Step 3: Preparation of 4-[3-(methoxycarbonylmethyl-aminocarbonyl)-4-nitro-phenyl]-[1,4]diazepane-1-carboxylic acid tert-butyl ester

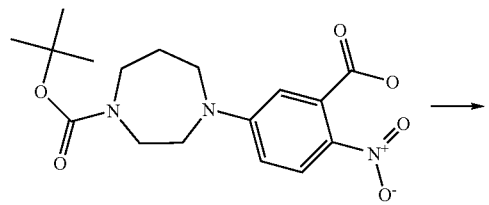

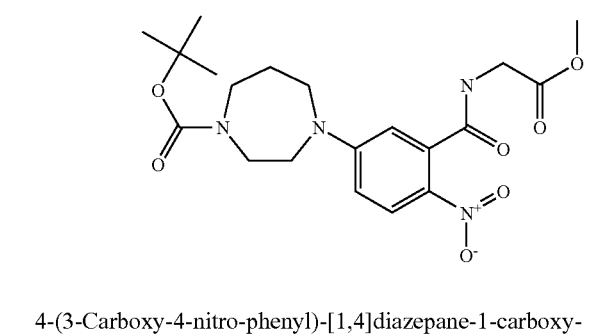

4-(3-Carboxy-4-nitro-phenyl)-[1,4]diazepane-1-carboxylic acid tert-butyl ester (37.27 g, 102 mmol) and 107.1 mmol of glycine methyl ester hydrochloride salt were suspended in methylene chloride. To this suspension was added 102 mmol of N-hydroxybenzotriazole and the mixture was cooled with an ice-water bath. Triethylamine (214 mmol) was added, effecting a solution. At this time 1.1 equivalents of 1-ethyl-3-(3-dimethyllaminopropyl)carbodiimide hydrochloride was added. This mixture was stirred at 0° C. for 1 hour and then at room temperature for 3 days. At this time, thin layer chromatography indicated the presence of 4-[3-(carboxymethyl-aminocarbonyl)-4-nitro-phenyl]-[1,4]diazepane-1-carboxylic acid tert-butyl ester. An additional 5.1 mmol each of glycine methyl ester hydrochloride salt and N-hydroxybenzotriazole as well as 10.3 mmol of triethylamine were added. The reaction mixture was stirred at room temperature for another 24 hour. At this time, the reaction mixture was diluted with methylene chloride, washed with water, with 10% (wt/vol) KHSO₄ solution, with water again, with saturated sodium bicarbonate aqueous solution, with water again, and finally with brine. The methylene chloride solution was concentrated to dryness in vacuo, resulting in a dark brown oil. The oil was purified by flash column chromatography: the column was loaded with a methylene chloride solution, followed by elution with ethyl acetate:hexane (7:3), and then finally with ethyl acetate. In this manner, fractions were collected and concentrated in vacuo to provide 42.05 g (94.4%) of 4-[3-(methoxycarbonylmethyl-aminocarbonyl)-4-nitro-phenyl]-[1,4]diazepane-1-carboxylic acid tert-butyl ester.

Step 4: Preparation of 4-[4-amino-3-(methoxycarbonylmethyl-aminocarbonyl)-phenyl]-[1,4]diazepane-1-carboxylic acid tert-butyl ester

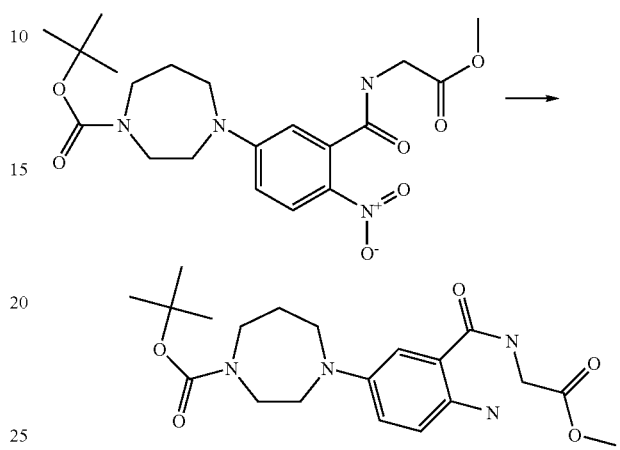

4-[3-(Methoxycarbonylmethyl-aminocarbonyl)-4-nitro-phenyl]-[1,4]diazepane-1-carboxylic acid tert-butyl ester (38.4 g) was dissolved in methanol and 4 g of 10% (wt/wt) palladium on carbon catalyst was added with water (1000 mL) under a nitrogen atmosphere. The mixture was then degassed before stirring under 1 atmosphere of hydrogen gas at room temperature for approximately 8 hours. At this time, the reaction mixture was filtered through celite and washed with copious volumes of methanol. The filtrate was concentrated in vacuo, To the residue was added acetonitrile before evaporation of the solvent. To give 4-[4-amino-3-(methoxycarbonylmethyl-aminocarbonyl)-phenyl]-[1,4]diazepane-1-carboxylic acid tert-butyl ester as a dark green oil: 34.05 g (95%).

Step 5: Preparation of 4-(3-methoxycarbonylmethyl-4-oxo-3,4-dihydro-quinazolin-6-yl)-[1,4]diazepane-1-carboxylic acid tert-butyl ester

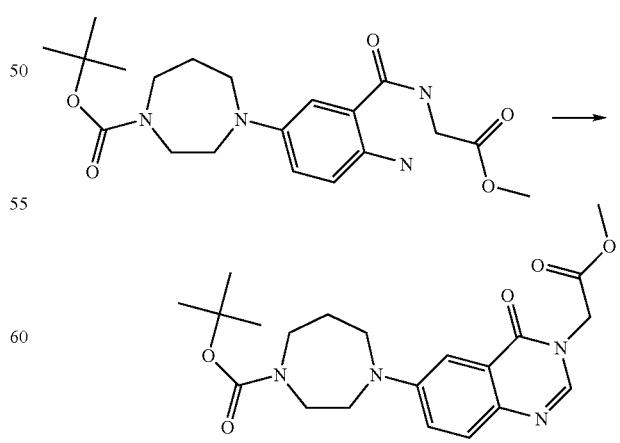

4-[4-Amino-3-(methoxycarbonylmethyl-carbamoyl)-phenyl]-[1,4]diazepane-1-carboxylic acid tert-butyl ester (30.6 g) was treated with 375 mL of triethylorthoformate at 125° C. with stirring for 18 hours. At this time, reaction mixture was concentrated in vacuo and the resulting residue was taken up in ethyl acetate and water. The organic phase was washed thrice with 10% $KHSO_4$ aqueous solution, once with water, once with brine. The organic layer was then dried over magnesium sulfate and was filtered. The filtrate was concentrated in vacuo. The product was purified by flash column chromatography (500 g of silica) eluting with 60% to 70% ethyl acetate in hexane. Appropriate fractions were collected and evaporated to dryness. The resulting residue was dissolved in diethyl ether and re-evaporated; this dissolution and re-evaporated was repeated using pentane. All solids obtained as foams were pooled, resulting in a total yield of 15.56 g of 4-(3-methoxycarbonylmethyl-4-oxo-3,4-dihydro-quinazolin-6-yl)-[1,4]diazepane-1-carboxylic acid tert-butyl ester.

Step 6: Preparation of 4-(3-carboxymethyl-4-oxo-3,4-dihydro-quinazolin-6-yl)-[1,4]diazepane-1-carboxylic acid tert-butyl ester

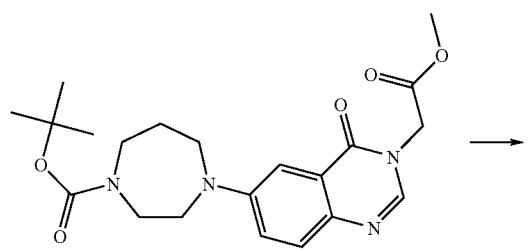

4-(3-Methoxycarbonylmethyl-4-oxo-3,4-dihydro-quinazolin-6-yl)-[1,4]diazepane-1-carboxylic acid tert-butyl ester (11.4 g) was dissolved in 140 mL of tetrahydrofuran and 50 mL of water. To this mixture was added drop-wise 2.3 g of lithium hydroxide monohydrate dissolved in 90 mL of water. This mixture was stirred overnight at room temperature. At this time, the reaction mixture was concentrated in vacuo. Water was added and the mixture was cooled with an ice bath. The reaction mixture was acidified to pH 4 by addition of 10% KHSO4 (wt./vol) aqueous solution, resulting in a precipitate, which was filtered and washed with water. After drying in a vacuum oven, 7.5 g of a solid were obtained. The remaining filtrate was concentrated in vacuo and triturated with pentane. This resulted in 2.5 g of solid. The solids were combined to give 10 g of 4-(3-carboxymethyl-4-oxo-3,4-dihydro-quinazolin-6-yl)-[1,4]diazepane-1-carboxylic acid tert-butyl ester.

Step 7: Preparation of (4-oxo-6-piperazin-1-yl-4H-quinazolin-3-yl)-acetic acid hydrochloride salt

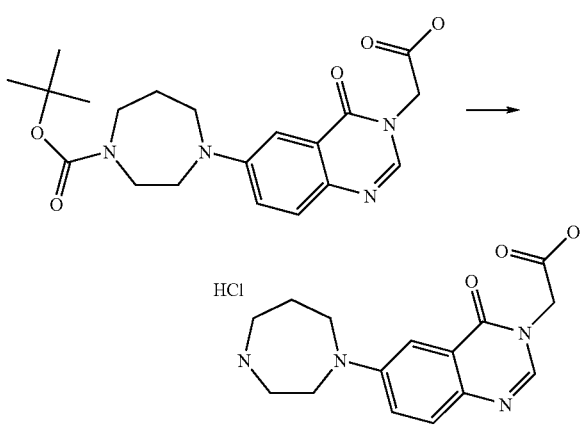

4-(3-Carboxymethyl-4-oxo-3,4-dihydro-quinazolin-6-yl)-[1,4]diazepane-1-carboxylic acid tert-butyl ester (9.8 g) was suspended in 20 mL of dioxane. To this suspension was added 4N HCl/dioxane solution (100 mL) and 20 mL of dioxane; the mixture was stirred at room temperature for 3 hours. At this time, the solvent was removed by concentration of the reaction mixture in vacuo, and to the residue was added tetrahydrofuran. The mixture was again concentrated in vacuo. The residue was triturated with dry diethyl ether, filtered and washed with dry diethyl ether. In this manner, 14.74 g of a solid was obtained. This solid was used without further purification.

Step 8: Preparation of 4-(3-carboxymethyl-4-oxo-3,4-dihydro-quinazolin-6-yl)-[1,4]diazepane-1-carboxylic acid 9H-fluoren-9-ylmethyl ester

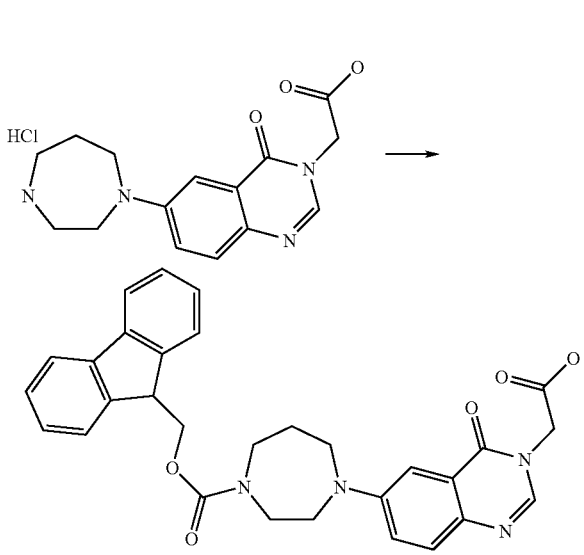

The crude material obtained in the previous step, (4-oxo-6-piperazin-1-yl-4H-quinazolin-3-yl)-acetic acid hydrochloride salt, was dissolved in 10% (wt/vol) aqueous sodium bicarbonate (pH 9.5) and cooled in an ice bath. A solution of 8.16 g of carbonic acid 2,5-dioxo-pyrrolidin-1-yl ester 9H-fluoren-9-ylmethyl ester dissolved in 60 mL of dioxane was added drop-wise during 1 hour. The mixture was then stirred at 0° C. for 1 h and then at room temperature for 1 hour. At this time, the reaction mixture had become a thick suspension. This mixture was diluted with water (1500 mL), resulting in a gel. The mixture was cooled with an ice bath and acidified to pH3 with concentrated hydrochloric acid with mechanical stirring. The mixture was then filtered and washed with water. The solid was dried in an vacuum oven, resulting in 12.5 g of solid. The solid was triturated with hot ethyl acetate. Upon cooling to room temperature, it was possible to collect by filtration 11.65 g of 4-(3-carboxymethyl-4-oxo-3,4-dihydro-quinazolin-6-yl)-[1,4]diazepane-1-carboxylic acid 9H-fluoren-9-ylmethyl ester.

Preparation of intermediate 4. The intermediate utilized in example 9,4-(7-carboxymethyl-6-oxo-6,7-dihydro-1H-purin-2-yl)-piperazine-1-carboxylic acid 9H-fluoren-9-ylmethyl ester (Fmoc-Pdp-OH) was prepared as follows.

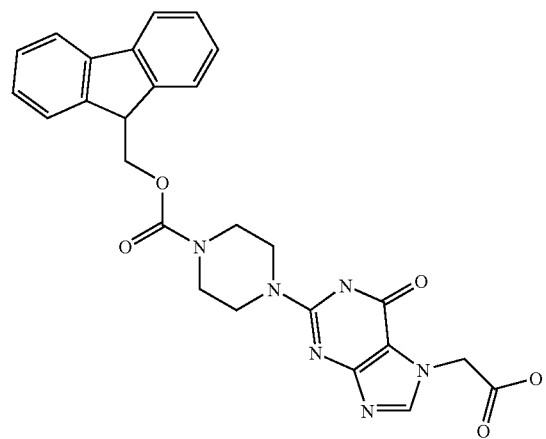

Synthesis Scheme

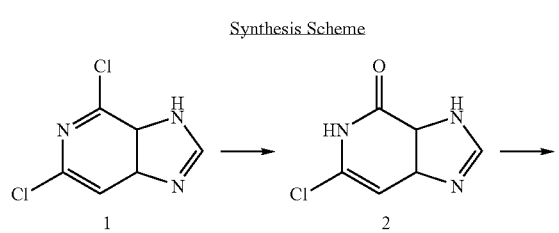

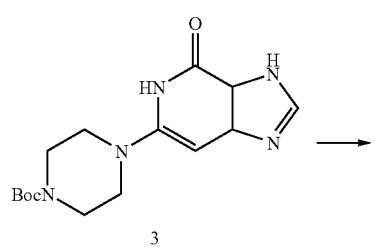

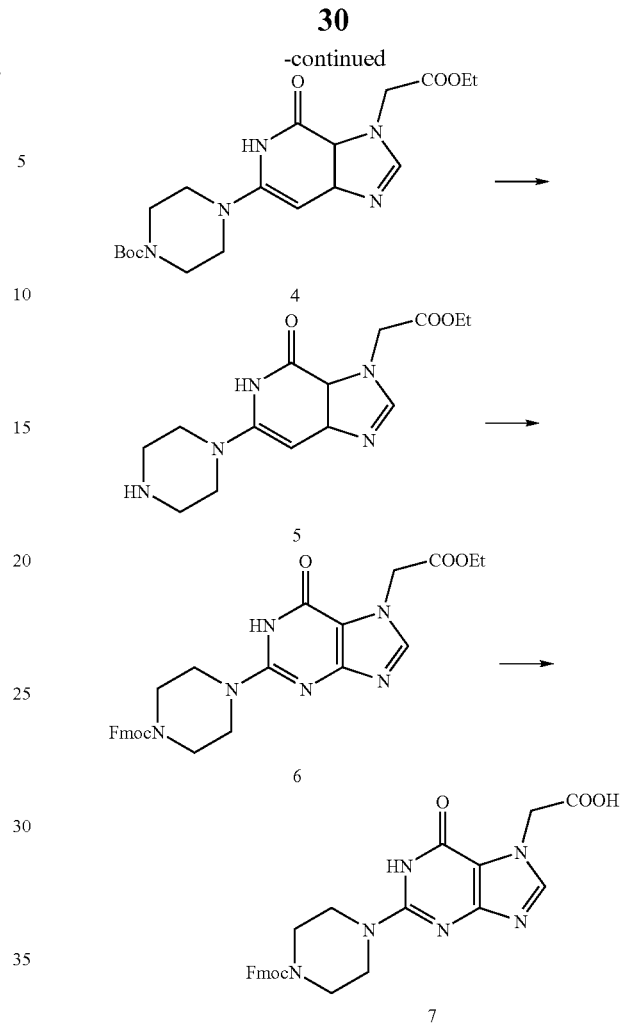

Step 1: The preparation of 6-chloro-3,5-dihydro-imidazo[4,5-c]pyridin-4-one, 2

An aqueous NaOH solution (2 equiv.) was added to a solution of 4,6-dichloro-3,5-dihydro-imidazo[4,5-c]pyridine in water. The reaction mixture was stirred at 90° C. until the completion of the reaction (monitored by TLC). The reaction mixture was allowed to cool down to room temperature and filtered to give light yellow residue. The residue was dissolved in water and acidified to pH 3-4 and was filtered to give 2.

Step 2: The preparation of 4-(4-oxo-4,5-dihydro-3H-imidazo[4,5c]pyridin-6-yl)piperazine-1-carboxylic acid tert-butyl ester, 3

To a solution of 6-chloro-3,5-dihydro-imidazo[4,5-c]pyridin-4-one, 2 in ethylene glycol monomethyl ether was added Boc-piperazine (1.1 equiv.). The reaction mixture was stirred under reflux overnight and then filtered to give the solid. The solid was washed with water to afford 3.

Step 3: The preparation of 4-(3-ethoxycarbonylmethyl-4-oxo-4,5-dihydro-3H-imidazo[4,5-c]pyridin-6-yl)-piperazine-1-carboxylic acid tert-butyl ester, 4

ClCH$_2$COOEt (1 equiv.) in dimethylforamide was added drop-wise to a solution of 4-(4-oxo-4,5-dihydro-3H-imidazo

[4,5-c]pyridin-6-yl)piperazine-1-carboxylic acid tert-butyl ester, 3 and potassium carbonate (0.8 equiv.) in dimethylforamide. The solution was stirred overnight. The mixture was then diluted with water and extracted with methylene chloride. The combined organic layers were dried over magnesium sulfate, and the solvents were evaporated. The product was further purified over a silica column chromatography, eluting with ethyl acetate, to give 4 as a solid.

Step 4: The preparation of (4-oxo-6-piperazin-1-yl-4, 5-dihydro-imidazo[4,5-c]pyridin-3-yl)-acetic acid ethyl ester, 5

4-(3-ethoxycarbonylmethyl-4-oxo-4,5-dihydro-3H-imidazo[4,5-c]pyridin-6-yl)-piperazine-1-carboxylic acid tert-butyl ester, 4 was dissolved in dry methylene chloride at room temperature under $N_2$. $CF_3COOH$ (5 equiv.) was added, and the reaction mixture was stirred for 1.5 h. Then methylene chloride was removed in vacuo and the residue was used in the next step without further purification.

Step 5: The preparation of 4-(3-ethoxycarbonylmethyl-4-oxo-4,5-dihydro-3H-imidazo[4,5-c]pyridin-6-yl)-piperazine-1-carboxylic acid 9H-fluoren-9-ylmethyl ester, 6

To a solution of (4-oxo-6-piperazin-1-yl-4,5-dihydro-imidazo[4,5-c]pyridin-3-yl)-acetic acid ethyl ester, 5 in methylene chloride was added potassium carbonate (2 equiv.) and a little tetrahydrofuran/water (1:1). The mixture was stirred for 20 min. Then to the solution was added carbonic acid 2,5-dioxo-pyrrolidin-1-yl ester 9H-fluoren-9-ylmethyl dissolved in methylene chloride. The mixture was stirred overnight at room temperature, filtered, and the solvent was removed to give a residue which was purified by silica gel chromatography to afford 6.

Step 6: The preparation of 4-(3-carboxymethyl-4-oxo-4,5-dihydro-3H-imidazo[4,5-c]pyridin-6-yl)-piperazine-1-carboxylic acid 9H-fluoren-9-ylmethyl ester, 7

Aqueous 1N LiOH (5 equiv.) was added to a solution of 4-(3-ethoxycarbonylmethyl-4-oxo-4,5-dihydro-3H-imidazo[4,5-c]pyridin-6-yl)-piperazine-1-carboxylic acid 9H-fluoren-9-ylmethyl ester, 6 dissolved in tetrahydrofuran/water (7:1) at room temperature Then the mixture was stirred at room temperature for 10 min. The solution was acidified (pH=3~4) with 1 N HCl. Tetrahydrofuran was then added. Purification by silica gel chromatography gave 7.

Preparation of intermediate 5. The intermediate utilized in example 10:4-(7-carboxymethyl-6-oxo-6,7-dihydro-1H-purin-2-yl)-piperazine-1-carboxylic acid 9H-fluoren-9-ylmethyl ester (Fmoc-Ppa-OH) was prepared as follows.

Synthesis Scheme:

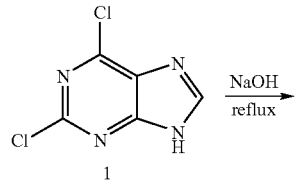

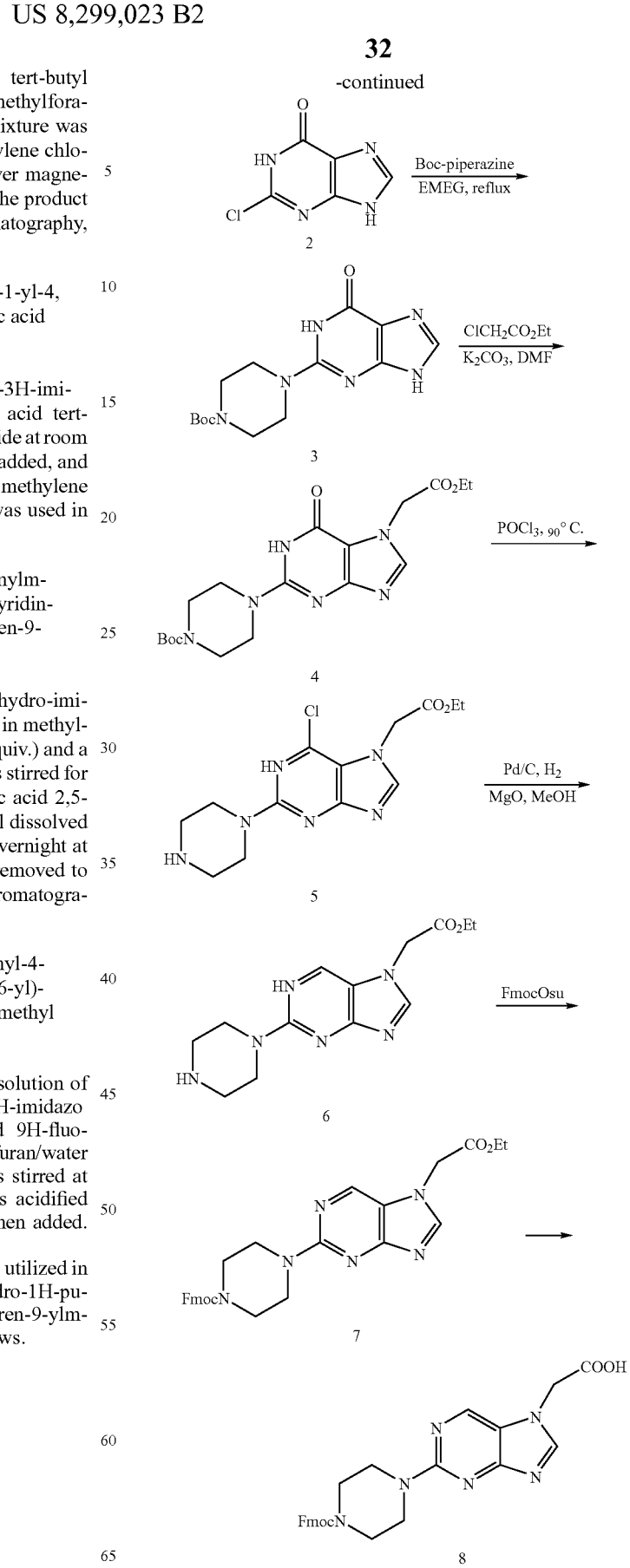

Step 1. The synthesis of 2-chloro-1,7-dihydro-purin-6-one, 2

A mixture of compound 2,6-dichloro-7H-purine, 1 (60 g, 300 mL) and NaOH (30 g) in water was stirred at 100° C. for 5 h, then the reaction mixture was cooled to room temperature and was filtered. The solid was washed with ethyl acetate, then dissolved in water, treated with aq. HCl solution until pH was adjusted to 4. A precipitate formed overnight, the solid was filtered, was washed with a little water, and was dried to give 2.

Step 2. The synthesis of 4-(6-oxo-6,7-dihydro-1H-purin-2-yl)-piperazine-1-carboxylic acid tert-butyl ester, 3

A mixture of 2-chloro-1,7-dihydro-purin-6-one, 2 (5 g), piperazine (5.5 g) and 30 mL ethylene glycol monomethyl ether was refluxed overnight, then cooled to room temperature. The solvent was removed by filtration, the solid was washed by water to give 3.

Step 3. The synthesis of 4-(7-ethoxycarbonylmethyl-6-oxo-6,7-dihydro-1H-purin-2-yl)-piperazine-1-carboxylic acid tert-butyl ester, 4

A mixture of 4-(6-oxo-6,7-dihydro-1H-purin-2-yl)-piperazine-1-carboxylic acid tert-butyl ester, 3 (1 g), potassium carbonate and dimethylforamide was stirred at room temperature for 2 h, then the solution of $ClCH_2COOEt$ (0.38 g/5 mL dimethylforamide) was added drop-wise into the reaction mixture, After stirring for 15 h, the solution was then partitioned between ethyl acetate and water. The ethyl acetate solution was washed with water, then it was dried over sodium sulfate and filtered, evaporated under reduced pressure, and purification of the residue by use of column chromatography to give 4.

Step 4. The synthesis of (6-chloro-2-piperazin-1-yl-purin-7-yl)-acetic acid ethyl ester, 5

A mixture of 0.6 g of 4-(7-ethoxycarbonylmethyl-6-oxo-6,7-dihydro-1H-purin-2-yl)-piperazine-1-carboxylic acid tert-butyl ester, 4 in 20 mL of $POCl_3$ was heated to 80° C. for 4 h. The excess $POCl_3$ was removed by concentration in vacuo. The residue was poured into ice water. The pH was adjusted by 5N NaOH. The solution was extracted with methylene chloride. The organic phase was concentrated in vacuo to afford 5.

Step 5. The synthesis of (2-piperazin-1-yl-purin-7-yl)-acetic acid ethyl ester, 6

To a solution of 1.47 g of (6-chloro-2-piperazin-1-yl-purin-7-yl)-acetic acid ethyl ester, 5 in 100 mL of methanol, was added 400 mg of 10% Pt/C and 1.1 g MgO under $N_2$, then the reaction was hydrogenated for 4 h. The catalyst and MgO were filtered and washed with methanol. Evaporation of the methanol in vacuo gave 6.

Step 6. The synthesis of 4-(7-ethoxycarbonylmethyl-7H-purin-2-yl)-piperazine-1-carboxylic acid 9H-fluoren-9-yl ester, 7

18 mg of (2-piperazin-1-yl-purin-7-yl)-acetic acid ethyl ester, 6 and 20 mg of Fmoc-OSu were dissolved in 20 mL of methylene chloride, the reaction mixture was stirred for 5 h, then filtered and methylene chloride was removed in vacuo, the resulting solid was purified by column chromatography to give 7.

Step 7. The synthesis of 4-(7-carboxymethyl-7H-purin-2-yl)-piperazine-1-carboxylic acid 9H-fluoren-9-ylmethyl ester, 8

A mixture of 0.1 mL of 1N LiOH and 10 mg of 4-(7-ethoxycarbonylmethyl-7H-purin-2-yl)-piperazine-1-carboxylic acid 9H-fluoren-9-yl ester in 2.1 mL of tetrahydrofuran/water (7/1) at room temperature was stirred for 10 min. 3N HCl was added to adjust the pH to 3-4, and the mixture was evaporated in vacuo to give 8.

Preparation of intermediate 6. The intermediate utilized in example 11 4-(6-amino-7-carboxymethyl-7H-purin-2-yl)-piperazine-1-carboxylic acid 9H-fluoren-9-yl ester (Fmoc-Appa-OH) was prepared as follows.

Synthesis Scheme

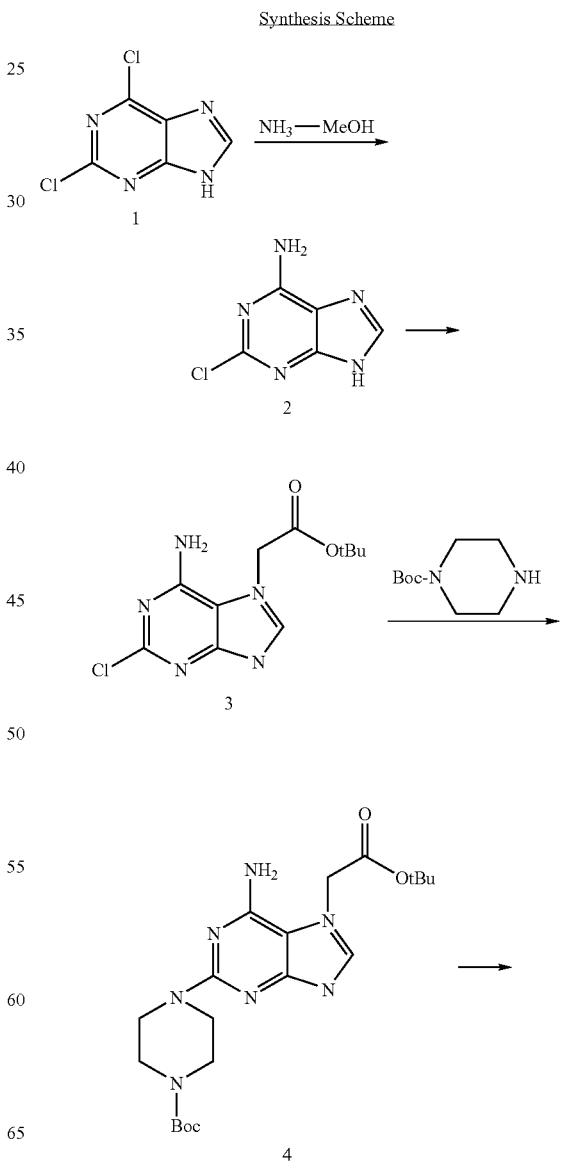

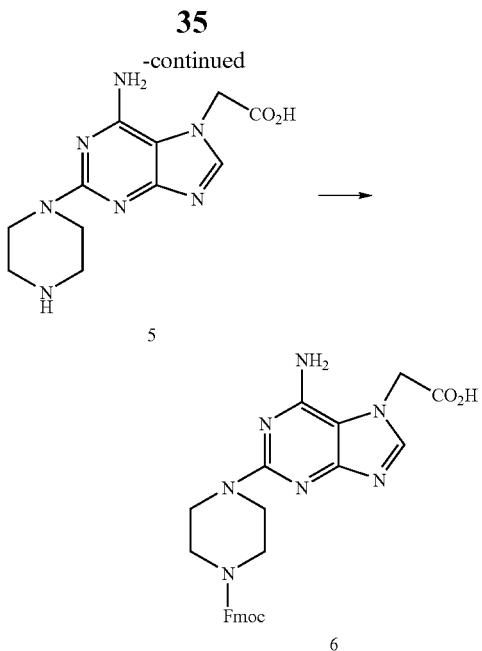

Step 4 The preparation of 4-(6-amino-7-carboxymethyl-7H-purin-2-yl)-piperazine-1-carboxylic acid 9H-fluoren-9-ylmethyl ester 6

To a stirred mixture of crude 4 (7 g) in $CH_2Cl_2$ (200 ml) was gradually added $CF_3CO_2H$ (200 ml). The mixture was stirred overnight. Then potassium carbonate was added to adjust the pH to 7.5. Saturated aqueous sodium bicarbonate solution was then added to keep the pH 8-9. After the adjustment of the pH, Fmoc-OSuc (10 g) in THF was added to the mixture and it was stirred for further 5 hours. THF was evaporated and the mixture was washed with ethyl acetate (150 ml×2). The water layer was tuned the pH to 3 with 2N HCl and then extracted with dichloromethane (150 ml×7). The organic layer was dried over $Na_2SO_4$ and concentrated to give the crude product (0.5 g). Further purification by preparative HPLC afforded 4-(6-amino-7-carboxymethyl-7H-purin-2-yl)-piperazine-1-carboxylic acid 9H-fluoren-9-ylmethyl ester, 6 (50 mg).

Preparation of intermediate 7. The intermediate utilized in example 12 5-(3-carboxymethyl-4-oxo-3,4-dihydroquinazolin-6-yl)-2-aza-bicyclo[2.2.1]heptane-2-carboxylic acid 9H-fluoren-9-ylmethyl ester (Fmoc-Bqa-OH) was prepared as follows.

Step 1 The preparation of 6-amino-2-chloropurine 2

2,6-Dichloro-purine, 1 (30 g, 0.159 mol) was dissolved in a $NH_3$/MeOH solution (300 ml, 30 wt % $NH_3$ in MeOH). The reaction mixture was stirred in an autoclave and heated to 100° C. for 48 h. After cooling, the mixture was filtered and the solid was washed with methanol. Then it was dried in vacuum to afford 2 as a pale yellow powder (16 g, yield 60%).

Step 2 The preparation of (6-amino-2-chloro-purin-7-yl)-acetic acid 1,1-dimethylethyl ester 3

A mixture of compound 6-amino-2-chloropurine (55 g, 0.324 mol), Tetra-n-butylammonium fluoride (8.6 g, 32.4 mmol) and $K_2CO_3$ (53.7 g, 0.389 mol) in DMSO (600 ml) was stirred at 0° C. Tert-butyl 2-bromoacetate was added dropwise. When the reaction was completed, the mixture was poured into brine and extracted with ethyl acetate (300 ml×5). The combined organic layers were washed with brine for 4-5 times, then dried over $Na_2SO_4$ and evaporated. The residue was purified by chromatography eluting with $CH_2Cl_2$:$CH_3OH$ (8:1) to afford 3, 6-amino-2-chloro-purin-7-yl)-acetic acid 1,1-dimethylethyl ester (5 g, yield 6%).

Step 3 The preparation of 4-(6-amino-7-tert-butoxycarbonylmethyl-7H-purin-2-yl)piperazine-1-carboxylic acid tert-butyl ester 4

To a stirred mixture of (6-amino-2-chloro-purin-7-yl)-acetic acid 1,1-dimethylethyl ester, 3 (5 g, 17.6 mmol) in dimethylsulfoxide (50 ml) was added tert-butyl piperazine-1-carboxylate (10 g, 53.8 mmol) at 120° C. After the addition, the mixture was stirred for about 14 h. Water (100 ml) and ethyl acetate (100 ml) were added to the reaction mixture. The organic layers was then washed with $H_2O$ several times, dried with $Na_2SO_4$ and concentrated to give crude product 4-(6-amino-7-tert-butoxycarbonylmethyl-7H-purin-2-yl)-piperazine-1-carboxylic acid tert-butyl ester, 4 (7 g) which was not purified and used for the next reaction directly.

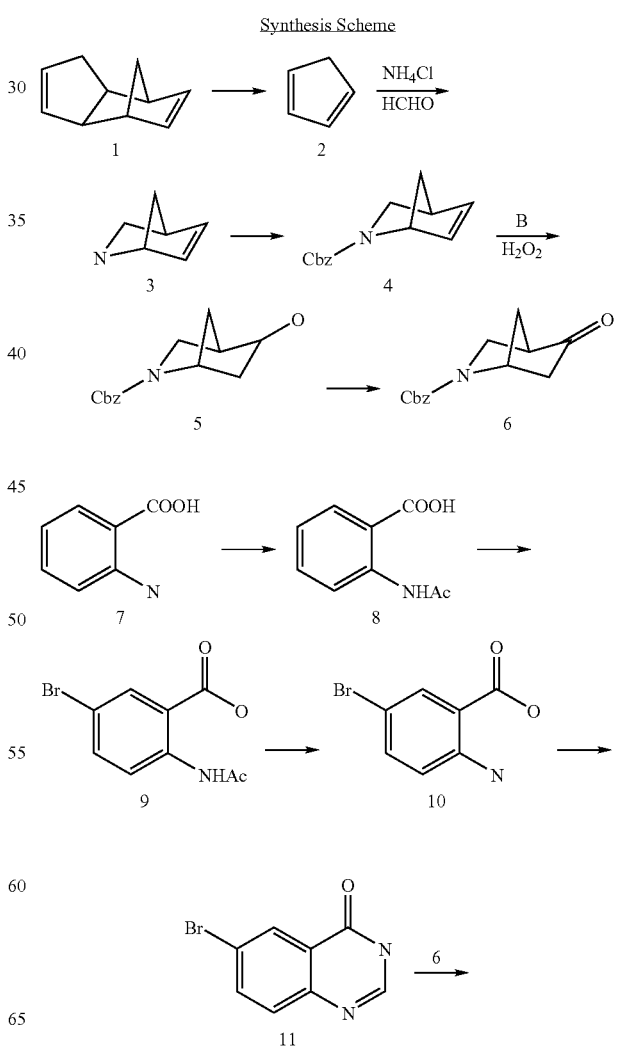

-continued

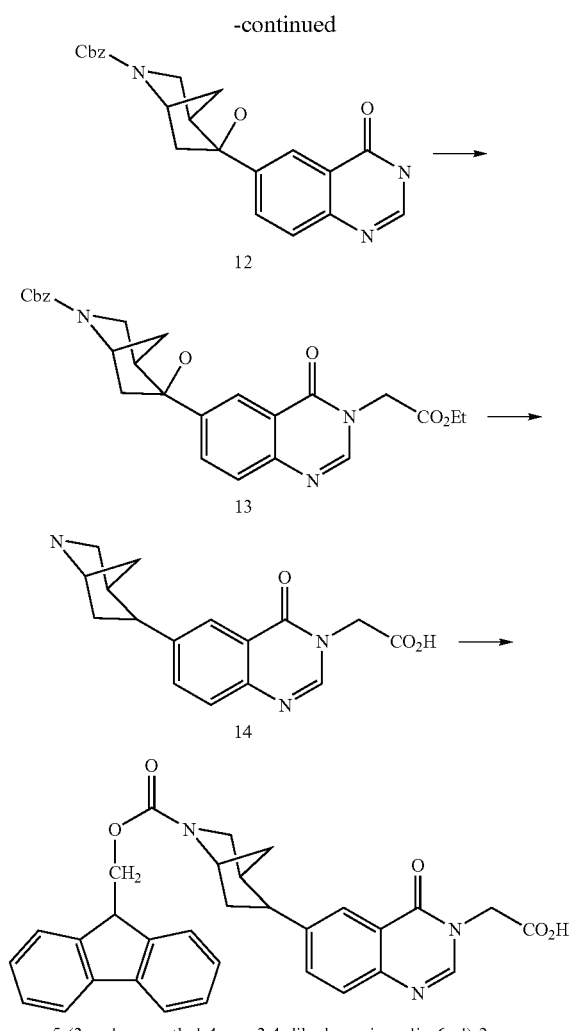

5-(3-carboxymethyl-4-oxo-3,4-dihydro-quinazolin-6-yl)-2-aza-bicyclo[2.2.1]heptane-2-carboxylic acid 9H-fluoren-9-yl methyl ester

Step 1 The synthesis of cyclopentadiene 2

Dicyclopentadiene (200 g, 1.513 mol) was distilled at 180° C. to give 150 g of 2. (yield: 75%).

Step 2 The synthesis of 2-azabicyclo[2.2.1]hept-5-ene 3 and 2-azabicyclo[2.2.1]hept-5-ene-2-carboxylic acid phenylmethyl ester 4

A mixture of cyclopentadiene, 2 (120 g, 1.82 mol), ammonium chloride (291.8 g, 5.46 mol), and 40% formaldehyde (221 mL, 2.73 mol) in water (1 L) was stirred at room temperature for 48 h. Then, to this mixture was added NaOH (220 g, 5.5 mol), CbzCl (310.5 g, 1.82 mol) and the mixture was stirred at room temperature overnight. The organic layer was separated and the water phase was extracted with twice with ethyl acetate. The organic layers were combined and dried over sodium sulfate, filtered and evaporated to dryness. The residue was purified by column chromatography on silica gel eluting with (petroleum ether/ethyl acetate=10:1) to give the product 4 as a clear oil (192 g, yield: 46%).

Step 3 The synthesis of endo-5-hydroxy-2-azabicyclo[2.2.1]heptane-2-carboxylic acid phenylmethyl ester 5

To a solution of 4 (50 g, 0.218 mol) in tetrahydrofuran (500 mL) was added $BH_3$ tetrahydrofuran (1 M, 218 mL) dropwise at 0° C. After addition, the mixture was stirred at room temperature for 2 h. The reaction was quenched by addition of water (130 mL), then NaOH (6 M, 130 mL) and water (30%, 130 mL) was added and the mixture was stirred at room temperature for 30 min. The tetrahydrofuran layer was separated and the water phase was extracted with ethyl acetate 3 times. The organic layers were combined, dried over sodium sulfate, filtered and evaporated to dryness. Purification by chromatography eluting with methylene chloride/ethyl acetate 2/1) gave 21.6 g of product 5 (yield: 40%)

Step 4 The synthesis of 5-oxo-2-azabicyclo[2.2.1]heptane-2-carboxylic acid phenylmethyl ester, 6

Jones reagent is prepared by dissolving chromium oxide (23.5 g) in concentrated sulfuric acid (21 mL) with cooling and then diluted with distilled water to give a total volume of 175 mL. To 5 (20 g, 0.08 mol) was added at room temperature Jones reagent until the color of the solution changed from green to orange yellow. The mixture was extracted with ethyl acetate and washed with water 3 times. The organic layers were combined and dried over sodium sulfate, filtered and evaporated to dryness to give 6 (17 g, yield: 85%).

Step 5 The synthesis of N-acetylantranilic acid, 8

A mixture of anthranilic acid (60 g, 0.44 mol) in acetic anhydride (60 g, 0.60 mol) was heated to 65° C. After 5 min, the mixture was refluxed at 120° C. for about 3 h. The reaction mixture was poured out into 500 mL water. The solid was filtered and dried to give the product 8 (68 g, yield: 87%)

Step 6 The synthesis of N-acetyl-5-bromo-anthranilic acid, 9

To a mixture of 8 (68 g, 0.38 mol) in acetic acid (500 mL) was carefully added bromine (70 g, 0.44 mol), then the mixture was stirred at room temperature for about 18 h. The reaction mixture was then poured out into water (500 mL) and filtered. The precipitate was washed with water several times. The solid was dried to give the product 9 (71 g, 72.4%)

Step 7 The synthesis of 5-bromo-anthranilic acid, 10

To a mixture of 9 (71 g, 0.275 mol) in 1,4-dioxane (400 mL) was added HCl (400 mL). The mixture was refluxed for 4 h at 110° C. Then the mixture was concentrated and added to 300 mL water. The mixture was filtered and the pH was adjusted to 6 with 2N NaOH, washed with water and dried to give 10 as a white solid (54.5 g, yield: 91.7%).

Step 8 The synthesis of 6-bromoquinzoline, 11

To a solution of 10 (54.5 g, 0.252 mol) in 500 mL of 2-methoxyethanol was added formamidine acetate (34.1 g, 0.328 mol). The reaction mixture was refluxed for 4 h, cooled to room temperature, and 500 mL of water was added. The resulting yellow precipitate was collected by filtration to give 11 (44.1 g, yield: 79%).

Step 9 The synthesis of 5-hydroxy-5-(4-oxo-3,4-dihydro-quinazolin-6-yl)-2-azabicyclo[2.2.1]heptane-2-carboxylic acid benzyl ester, 12

To a solution of 11 (20 g, 88.8 mmol) in tetrahydrofuran (500 mL) stirred at −78° C. was added MeLi (40 mL, 120.4 mmol) drop-wise. After addition, the reaction mixture was stirred at −78° C. for 10 min. Then to the above solution was added n-BuLi (46 mL, 2.5 M) drop-wise at −78° C. After addition, the mixture was stirred at −78° C. for 1 h. Then to the above reaction mixture was added 6 (21.8 g, 88.9 mmol), and the mixture was stirred at −78° C. for 2 h, and then quenched with water. The pH of the mixture was adjusted to 3 with 2N HCl, then extracted with ethyl acetate, dried over sodium sulfate, and evaporated to dryness. The residue was purified by column chromatography on silica gel eluting with methylene chloride/ethyl acetate 1/1 to methylene chloride/ethyl acetate/MeOH 1/1/0.1) to yield 20.8 g of 12 (59% yield).

Step 10 The synthesis of 5-(3-ethoxycarbonylmethyl-4-oxo-3,4-dihydroquinazolin-6-yl)-5-hydroxy-2-aza-bicyclo[2.2.1]heptane-2-carboxylic acid benzyl ester, 13

To a mixture of 12 (10 g, 25.6 mmol) in dimethylforamide (100 mL) was added $BrCH_2CO_2CH_2CH_3$ (5.55 g, 33.21 mmol). The mixture was stirred overnight at room temperature. The reaction was quenched by water and extracted with ethyl acetate. The combined organic layer was washed by water for 5 times and dried over sodium sulfate, and then concentrated in vacuo to give the product 13 (9.7 g, 80%).

Step 11 The synthesis of 5-(3-carboxymethyl-4-oxo-3,4-dihydro-quinazolin-6-yl)-2-aza-bicyclo[2.2.1]heptane-2-carboxylic acid 9H-fluoren-9-ylmethyl ester To a mixture of 13 (22.4 g, 47 mmol) in HOAc (448 mL) was added HI (268 mL). The mixture was heated to reflux at 120° C. overnight. The reaction mixture was evaporated and its pH was adjusted to 6-7 with potassium carbonate and $NaHCO_3$. Then 50 mL of tetrahydrofuran was added. To the mixture was added FmocCl (15.68 g, 61 mmol) and stirred at room temperature for 5 h. Then the reaction mixture was extracted with ethyl acetate and washed with water 3 times. The organic layer was dried over sodium sulfate, filtered and evaporated to dryness. Purification by chromatography (eluant:methylene chloride to methylene chloride/MeOH/HAc 8/1/0.1) gave 10.3 g of crude 5-(3-carboxymethyl-4-oxo-3,4-dihydro-quinazolin-6-yl)-2-aza-bicyclo[2.2.1]heptane-2-carboxylic acid 9H-fluoren-9-ylmethyl ester which was further purified by preparative HPLC to give 2.7 g of pure 5-(3-carboxymethyl-4-oxo-3,4-dihydro-quinazolin-6-yl)-2-aza-bicyclo[2.2.1]heptane-2-carboxylic acid 9H-fluoren-9-ylmethyl ester (11% yield in 2 steps).

Preparation of intermediate 8. The intermediate utilized in example 13: 4-(2-carboxymethyl-1-oxo-1,2-dihydro-isoquinolin-7-yl)-piperazine-1-carboxylic acid 9H-fluoren-9-ylmethyl ester 10 (Fmoc-Pipa-OH) was prepared as follows.

Synthesis Scheme

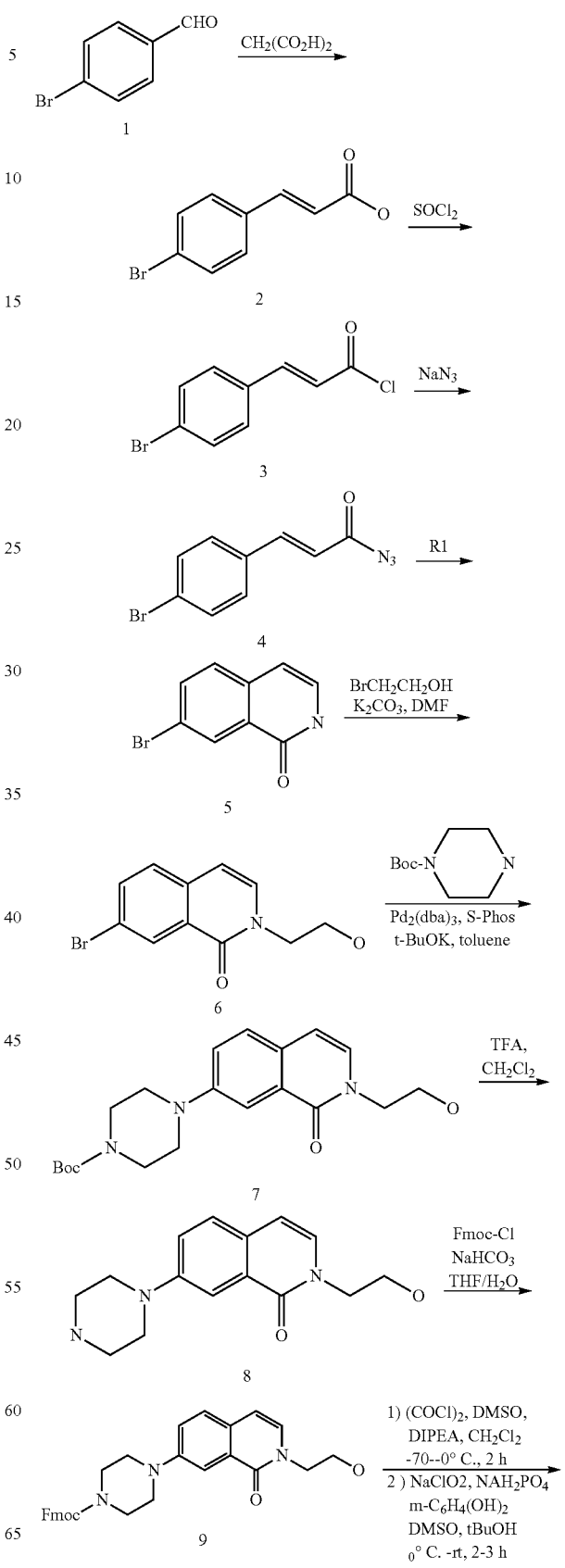

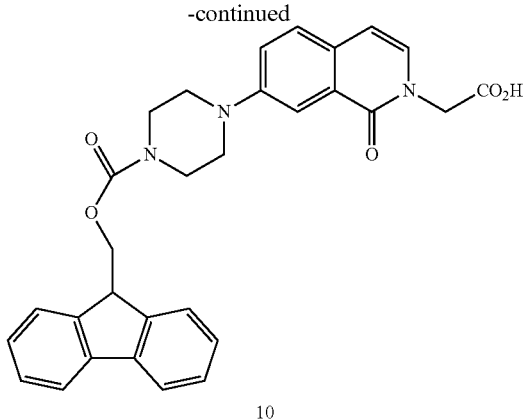

10

Step 1 The preparation of 4-bromocinnamic acid 2

A solution of 4-bromobenzaldehyde, 1 (110 g, 0.59 mol), malonic acid (112.5 g, 1.189 mol), piperidine (11 mL) in pyridine (350 mL) was heated to 80° C. for 1 h, then refluxed for 3 h. Then the reaction mixture was cooled to room temperature, poured into a large beaker filled with cold water, and then acidified (pH<3) by slowly adding 25 mL of concentrated hydrochloric acid. The resulting precipitate was filtered and washed with cold water. The crude product was dissolved in aqueous sodium hydroxide, acidified (pH<3) (1:1 hydrochloric acid/water), filtered, and washed (cold water). The solid was dried in vacuo (60-70° C.) to give 2 (118.8 g, 88%).

Step 2 The preparation of 4-bromocinnamoyl chloride, 3

A solution of compound 2 (113.8 g, 0.5 mol) in thionyl chloride was refluxed for 1.5 h. Then the mixture was concentrated in vacuo and the crude product 3 was obtained (126.9 g, 93%).

Step 3 The preparation of 4-bromocinnamoyl azide, 4

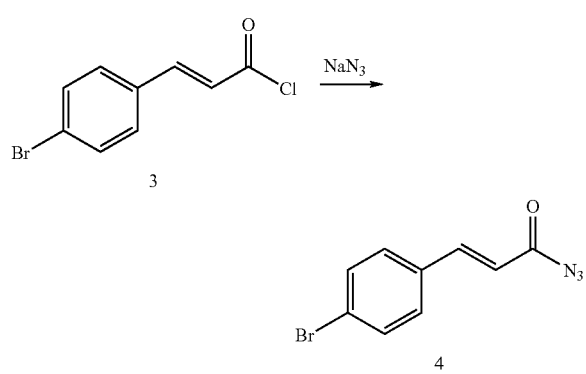

Sodium azide (67 g, 1 mol) was suspended in a mixture of water and acetone (300 mL, 1:1). The mixture was cooled to 0° C., a solution of compound 3 (126.9 g, 0.52 mol) in dry acetone (400 mL) was added at 5° C. The resulting mixture was stirred at 0-5° C. for 4 h and then poured into water (1.5 L). The precipitate was filtered off, washed with water, dried. Additional drying in vacuo over $P_2O_5$ gave 4 (130.3 g, 100%)

Step 4 The preparation of 7-bromo-2H-isoquinoline-1-one, 5

A solution of compound 4 (121.6 g, 0.48 mol) and tributylamine (177.9 g, 0.96 mol) in diphenylether (1.2 L) was headed to 210° C. for 2 hours under $N_2$. Then the mixture was cooled to room temperature, the precipitate was filtered, washed with hexane, and dried to give 5 (32 g, 30%)

Step 5 The preparation of 7-bromo-2-(2-hydroxyethyl)-isoquinolin-1-one, 6

A solution of compound 5 (19.8 g, 88.4 mmol), potassium carbonate (18.3 g, 133 mmol) and 2-bromoethanol (13.3 g, 106 mmol) in dimethylforamide (200 mL) was stirred at 80° C. for 12 h. Then the mixture was cooled to room temperature and poured into water. The mixture was extracted with ethyl acetate (three times 500 mL), dried (sodium sulfate), concentrated and purified by chromatography on silica gel to give 6 (16.2 g, 68%)

Step 6 The synthesis of 4-[2-(2-hydroxy-ethyl)-1-oxo-1,2-dihydro-isoquinolin-7-yl]piperazine-1-carboxylic acid tert-butyl ester, 7

A solution of compound 6 (6.8 g, 25.4 mmol), tert-butyl piperazine-1-carboxylate (5.68 g, 30.5 mmol), $Pd_2(dba)_3$ (775 mg, 0.85 mmol), S-Phos (1.16 g) and t-BuOK (5.7 g, 50.8 mmol) in toluene (100 mL) was heated to 90° C. under nitrogen overnight. Then the mixture was cooled to room temperature and filtered. The filtrate was concentrated, the residue was dissolved in methylene chloride, washed with water, dried (sodium sulfate), concentrated and purified by flash column chromatography (silica gel) to give 7 (6.1 g, 64%)

Step 7 The synthesis of compound 2-(2-hydroxy-ethyl)-7-piperazin-1yl-isoquinolin-1-one, 8

A solution of compound 7 (6 g, 16.1 mmol) in methylene chloride (20 mL) and trifluoroacetic acid (20 mL) was stirred at r.t for 1 h. Then the mixture was concentrated in vacuo to give the compound 8 (4.3 g, 98%)

Step 8 The synthesis of 4-[2-(2-hydroxy-ethyl)-1-oxo-1,2-dihydro-isoquinolin-7-yl]piperazine-1-carboxylic acid 9H-fluoren-9-ylmethyl ester 9

To a solution of sat. aqueous $NaHCO_3$ (80 mL), compound 8 (4.3 g, 15.7 mmol) in tetrahydrofuran was added chloroformic acid 9-fluorenylmethyl ester (1.5 eq.). The mixture was stirred for 2 h at room temperature, then concentrated. The residue was extracted with ethyl acetate, dried (sodium sulfate) and concentrated in vacuo to give 9 (4.6 g, yield 59%).

Step 9: The synthesis of target compound 4-(2-carboxymethyl-1-oxo-1,2-dihydro-isoquinolin-7-yl)-piperazine-1-carboxylic acid 9H-fluoren-9-ylmethyl ester 10

Dimethyl sulfoxide (1.42 g, 18.2 mmol) was added dropwise over 25 min to a solution of oxalyl chloride (1.73 g, 13.6 mmol) in 10 mL of methylene chloride at −70° C., then a solution of compound 9 (2.25 g, 4.54 mmol) in methylene chloride (20 mL) was added drop-wise over 50 min at −70° C. The reaction mixture was stirred at −55° C. for another 1 h, then N,N-diisopropylethylamine (3.52 g, 27.2 mmol) was added over 5 min. The mixture was stirred for 30 min at 0° C. A solution of 1M hydrochloric acid (50 mL) was added to the reaction mixture, then the mixture was extracted with methylene chloride (3 times with 100 mL), the combined organic phases were washed with sat. aqueous $NaHCO_3$, and water, dried (sodium sulfate), and concentrated in vacuo to give an aldehyde.

A solution of this aldehyde (2.2 g, 4.46 mmol), m-$C_6H_4$(OH)$_2$ (0.98 g, 8.92 mmol), aqueous $NaH_2PO_4$ (10 mL), t-BuOH (5 mL) in DMSO (50 mL) was cooled to 0° C., then aqueous $NaClO_2$ (5 mL) was added drop-wise. The reaction mixture was stirred for 3 hours at 0° C., added 100 mL of water, adjusted pH<5, extracted with ethyl acetate (3 times with 100 mL), dried (sodium sulfate), concentrated and purified by flash chromatography (silica gel) to give the target compound 4-(2-carboxymethyl-1-oxo-1,2-dihydro-isoquinolin-7-yl)-piperazine-1-carboxylic acid 9H-fluoren-9-ylmethyl ester, 10 (1.35 g, yield 58.7%).

The invention will now be further described in the Examples which follow, which are intended as an illustration only and do not limit the scope of the invention.

EXAMPLES

Example 1

Preparation of Fmoc-Linker-BHA Resin

Benzhydrylamine copolystyrene-1% divinylbenzene cross-linked resin (10.0 g, 9.3 mequiv, 100-200 ASTM mesh, Advanced ChemTech) was swelled in 100 mL $CH_2Cl_2$, filtered and washed successively with 100 ml each of $CH_2Cl_2$, 6% DIPEA/$CH_2Cl_2$ (two times), $CH_2Cl_2$ (two times). The resin was treated with p-((R,S)-α-(1-(9H-fluoren-9-yl)-methoxyformamido)-2,4-dimethoxybenzyl)-phenoxyacetic acid (Fmoc-Linker) (7.01 g, 13.0 mmole), N-hydroxybenzotriazole (2.16 g, 16.0 mmole), and diisopropyl-carbodiimide (2.04 ml, 13.0 mmol) in 100 mL 25% DMF/$CH_2Cl_2$ for 24 hours at room temperature. The resin was filtered and washed successively with 100 ml each of $CH_2Cl_2$ (two times), isopropanol (two times), DMF, and $CH_2Cl_2$ (three times). A Kaiser Ninhydrin analysis was negative. The resin was dried under vacuum to yield 16.12 g of Fmoc-Linker-BHA resin. A portion of this resin (3.5 mg) was subjected to Fmoc deprotection and quantitative UV analysis which indicated a loading of 0.56 mmol/g.

Example 2

Protocol for the Synthesis of Peptides by Applied Biosystem 433A Synthesizer Using Fluorenylmethyloxycarbonyl (Fmoc) Chemistry For a 0.25 mmol scale peptide synthesis by Applied Biosystem 433A synthesizer (Foster City, Calif.), the FastMoc 0.25 mmole cycles were used with either the resin sampling or non resin sampling, 41 mL reaction vessel. The Fmoc-amino acid resin was suspended with 2.1 g NMP, 2 g of 0.45M HOBT/HBTU in DMF and 2M DIEA, then transferred to the reaction vessel. The basic FastMoc coupling cycle was represented by "BADEIFD," wherein each letter represents a module (as defined by Applied Biosystems). For example:

B represents the module for Fmoc deprotection using 20% Piperidine/NMP and related washes and readings for 30 min (either UV monitoring or conductivity); A represents the module for activation of amino acid in cartridges with 0.45 M HBTU/HOBt and 2.0 M DIEA and mixing with $N_2$ bubbling; D represents the module for NMP washing of resin in the reaction vessel; E represents the module for transfer of the activated amino acid to the reaction vessel for coupling; I represents the module for a 10 minute waiting period with vortexing on and off of the reaction vessel; and F represents the module for cleaning the cartridge, coupling for approximately 10 minutes and draining the reaction vessel. Couplings were typically extended by addition of module "I" once or multiple times. For example, double couplings were run by performing the procedure "BADEIIADEIFD." Other modules were available such as c for methylene chloride washes and "C" for capping with acetic anhydride. Individual modules were also modifiable by, for example, changing the timing of various functions, such as transfer time, in order to alter the amount of solvent or reagents transferred. The cycles above were typically used for coupling one amino acid. For synthesizing tetra peptides, however, the cycles were repeated and strung together. For example, BADEIIADEIFD was used to couple the first amino acid, followed by BADEIIADEIFD to couple the second amino acid, followed by BADEIIADEIFD to couple the third amino acid, followed by BADEIIADEIFD to couple the fourth amino acid, followed by BIDDcc for final deprotection and washing.

Example 3

Preparation of H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-$NH_2$ (SEQ ID NO: 3) (PYY$_{3-36}$)

The above peptide was synthesized using Fmoc chemistry on an Applied Biosystem 433A synthesizer. The synthesizer was programmed for double coupling using the modules described in Example 2. The synthesis was carried out on a 0.25 mmole scale using the Fmoc-Linker-BHA resin (450 mg, 0.25 mmole) from Example 1. At the end of the synthesis, the resin was transferred to a reaction vessel on a shaker for cleavage. The peptide was cleaved from the resin using 13.5 mL 97% TFA/3% $H_2O$ and 1.5 mL triisopropylsilane for 180 minutes at room temperature. The deprotection solution was added to 100 mL cold $Et_2O$, and washed with 1 mL TFA and 30 mL cold $Et_2O$ to precipitate the peptide. The peptide was centrifuged 2×50 mL polypropylene tubes. The precipitates from the individual tubes were combined in a single tube and washed 3 times with cold $Et_2O$ and dried in a desiccator under house vacuum.

The crude material was purified by preparative HPLC on a Pursuit C18-Column (250×50 mm, 10 µm particle size) and eluted with a linear gradient of 2-70% B (buffer A: 0.1% TFA/$H_2O$; buffer B: 0.1% TFA/$CH_3CN$) in 90 min., flow rate 60 mL/min, and detection 220/280 nm. The fractions were collected and were checked by analytical HPLC. Fractions containing pure product were combined and lyophilized to yield 151 mg (15%) of a white amorphous powder. (ES)+- LCMS m/e calculated ("calcd") for $C_{180}H_{279}N_{53}O_{54}$ 4049.55. found 4050.40

Example 4

Preparation of Ac-Ile-Lys-Pqa-Arg-His-Tyr-Leu-Asn-Trp-Val-Thr-Arg-Gln-(NMe)Arg-Tyr-NH$_2$ (SEQ ID NO: 4)

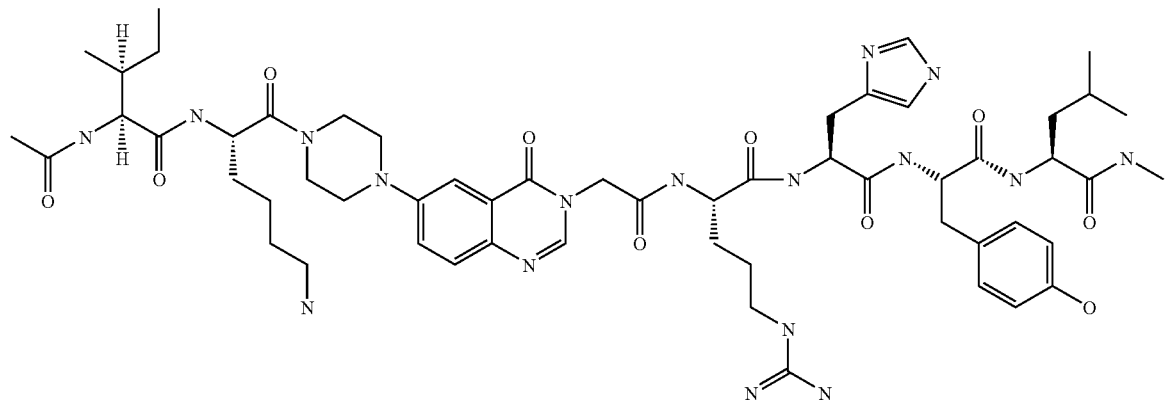

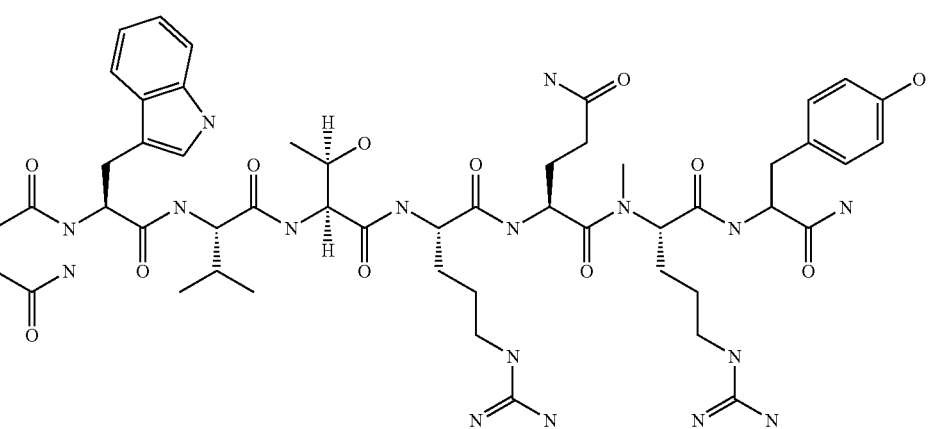

Fmoc-Linker-BHA resin (450 mg, 0.25 mmole) from Example 1 was subjected to solid phase synthesis and purification by following the general procedure described in Example 3 employing Fmoc-Pqa to yield 53 mg (9%) of white amorphous powder. (ES)+-LCMS m/e calculated ("calcd") for $C_{106}H_{156}N_{34}O_{22}$ 2257.21. found 2257.19.

Example 5

Preparation of Ac-Ile-Lys-Cba-Arg-His-Tyr-Leu-Asn-Trp-Val-Thr-Arg-Gln-(NMe)Arg-Tyr-NH$_2$ (SEQ ID NO: 5)

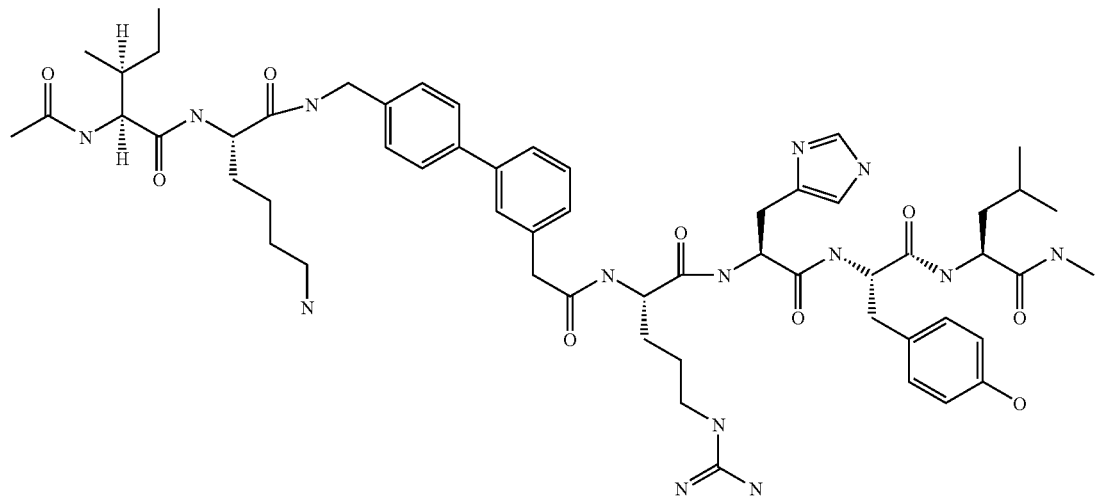

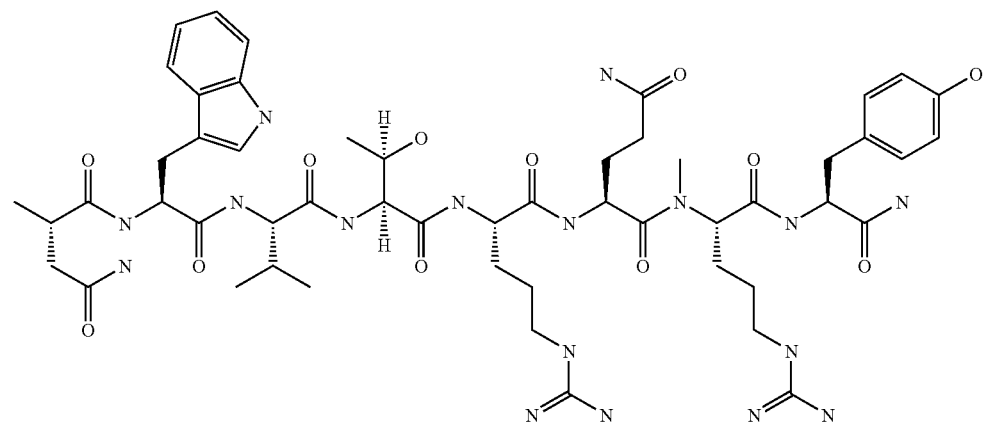

Fmoc-Linker-BHA resin (450 mg, 0.25 mmole) was prepared as described in Example 11 was subjected to solid phase synthesis and purification by following the general procedure in Example 3 and employing Fmoc-Cba to yield 18 mg (3.2%) of white amorphous powder. (ES)+-LCMS m/e calculated ("calcd") for $C_{107}H_{155}N_{31}O_{21}$ 2210.20. found 2210.19

Example 6

Preparation of Ac-Ile-Lys-Cip-Arg-His-Tyr-Leu-Asn-Trp-Val-Thr-Arg-Gln-(NMe)Arg-Tyr-NH₂ (SEQ ID NO: 6)

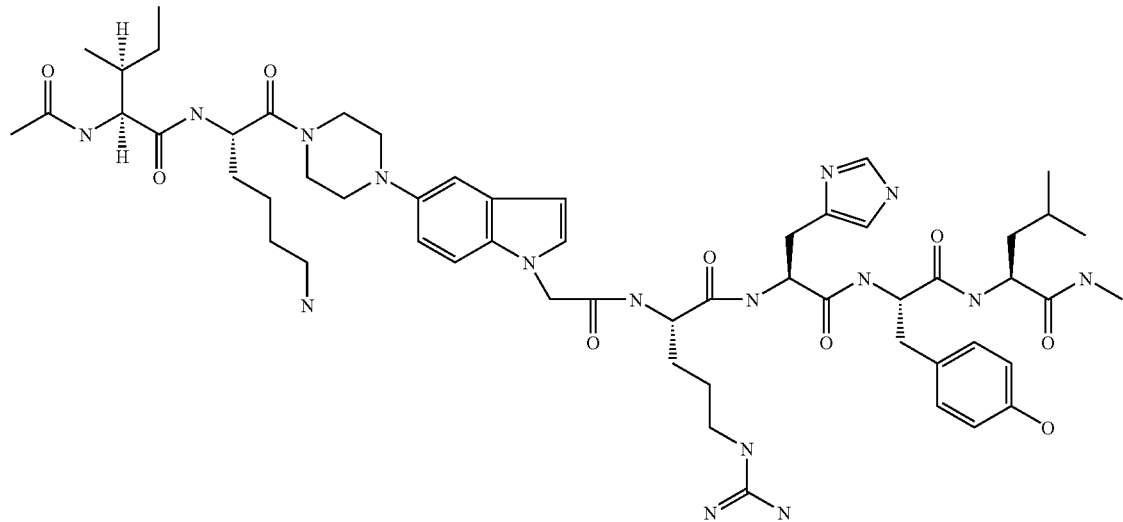

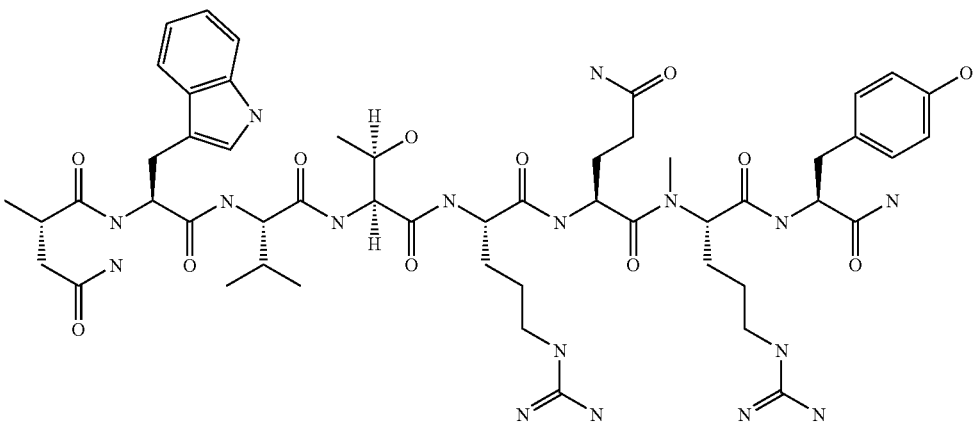

60

Fmoc-Linker-BHA resin (450 mg, 0.25 mmole) was prepared as described in Example 1 and was subjected to solid phase synthesis and purification by following the general procedure in Example 3, employing Fmoc-Cip to yield 16 mg (3%) of white amorphous powder. (ES)+-LCMS m/e calculated ("calcd") for $C_{106}H_{157}N_{33}O_{21}$ 2228.22. found 2228.21.

Example 7

Preparation of Ac-Ile-Lys-HomPqa-Arg-His-Tyr-Leu-Asn-Trp-Val-Thr-Arg-Gln-(NMe)Arg-Tyr-NH$_2$
(SEQ ID NO: 7)

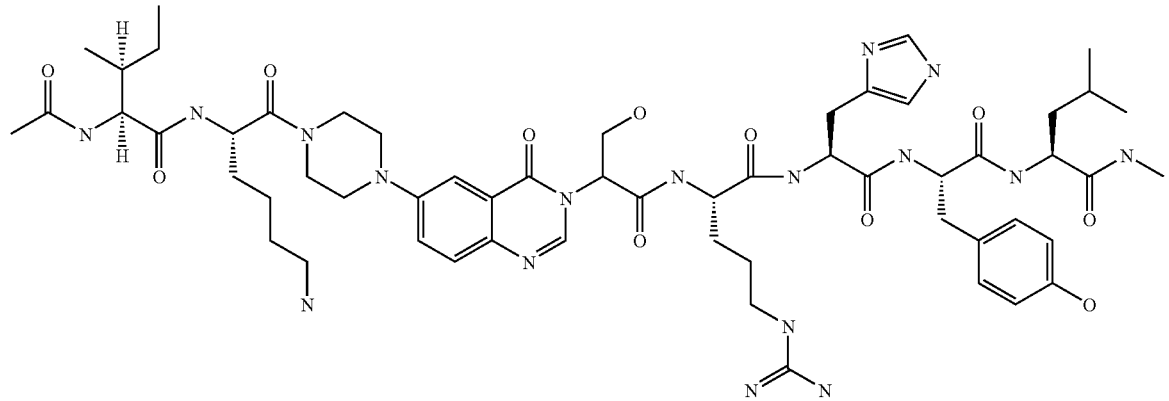

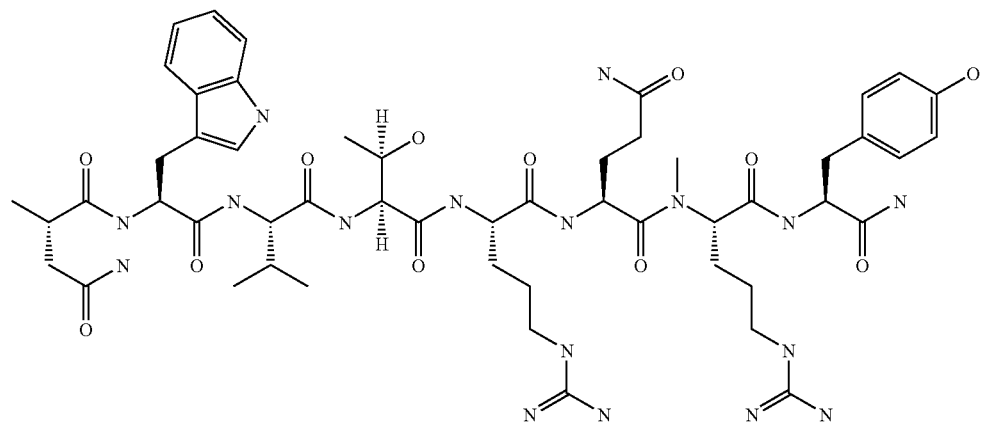

Fmoc-Linker-BHA resin (450 mg, 0.25 mmole) was prepared as described in Example 1 and was subjected to solid phase synthesis and purification by following the general procedure in Example 3, employing Fmoc-HomPQA to yield 11 mg (2%) of white amorphous powder. (ES)+-LCMS m/e calculated ("calcd") for $C_{107}H_{158}N_{34}O_{23}$ 2287.22. found 2287.24.

Example 8

Preparation of Ac-Ile-Lys-Dqa-Arg-His-Tyr-Leu-Asn-Trp-Val-Thr-Arg-Gln-(NMe)Arg-Tyr-NH$_2$ (SEQ ID NO: 8)

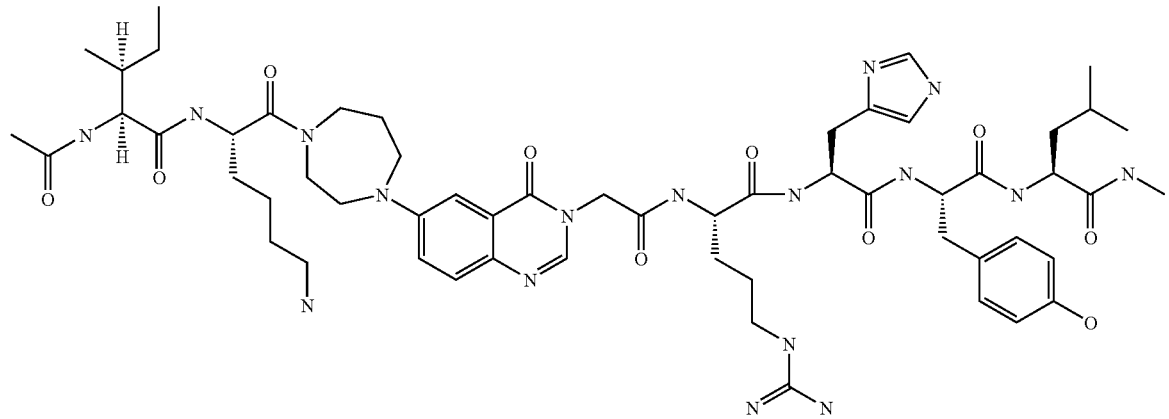

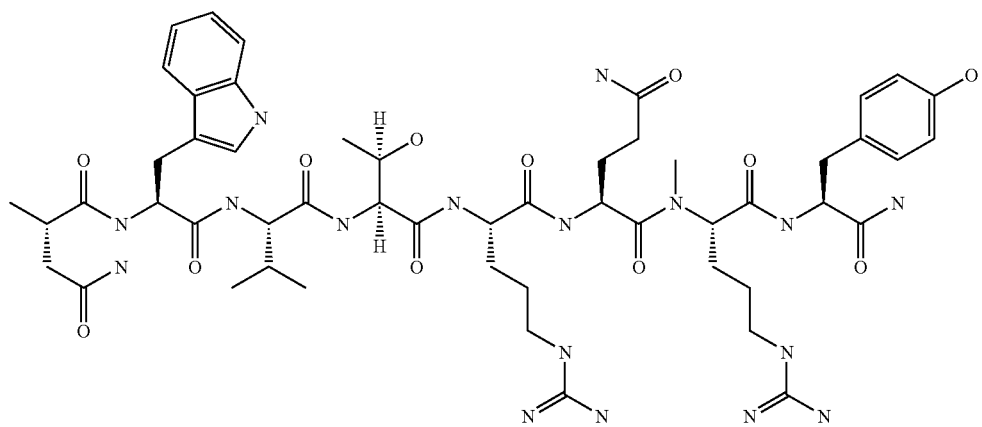

Fmoc-Linker-BHA resin (450 mg, 0.25 mmole) was prepared as described in Example 1 and was subjected to solid phase synthesis and purification by following the general procedure in Example 3, employing Fmoc-Dqa to yield 22 mg (4%) of white amorphous powder. (ES)+-LCMS m/e calculated ("calcd") for C$_{107}$H$_{158}$N$_{34}$O$_{22}$ 2271.23. found 2271.24.

Example 9

Preparation of Ac-Ile-Lys-Pdp-Arg-His-Tyr-Leu-
Asn-Trp-Val-Thr-Arg-Gln-(NMe)Arg-Tyr-NH$_2$ (SEQ
ID NO: 9)

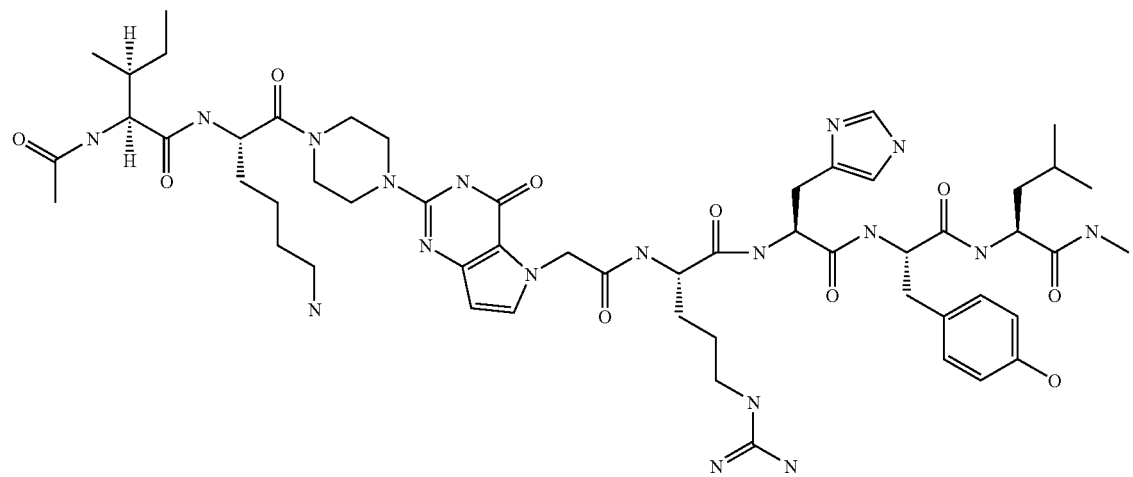

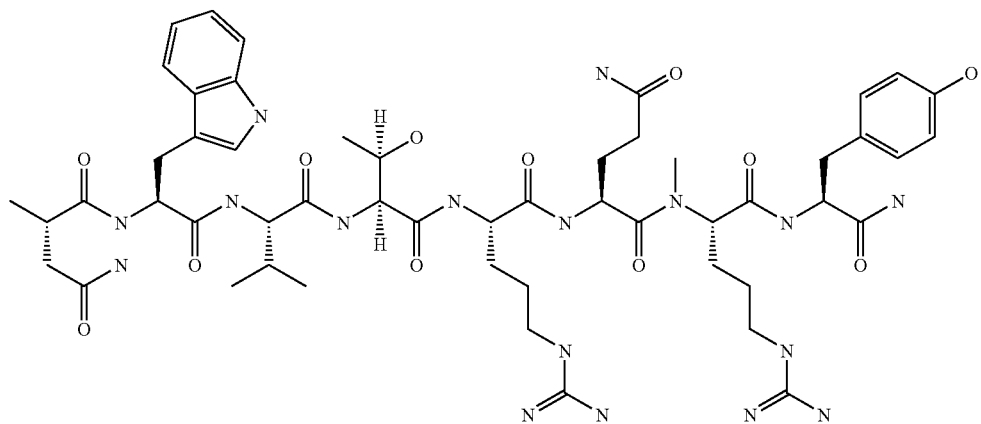

Fmoc-Linker-BHA resin (450 mg, 0.25 mmole was prepared as described in Example 1 and was subjected to solid phase synthesis and purification by following the general procedure in Example 3, employing Fmoc-Pdp to yield 17 mg (3%) of white amorphous powder.)+-LCMS m/e calculated ("calcd") for C$_{103}$H$_{154}$N$_{36}$O$_{22}$ 2247.21. found 2247.19.

Example 10

Preparation of Ac-Ile-Lys-Ppa-Arg-His-Tyr-Leu-Asn-Trp-Val-Thr-Arg-Gln-(NMe)Arg-Tyr-NH₂ (SEQ ID NO: 10)

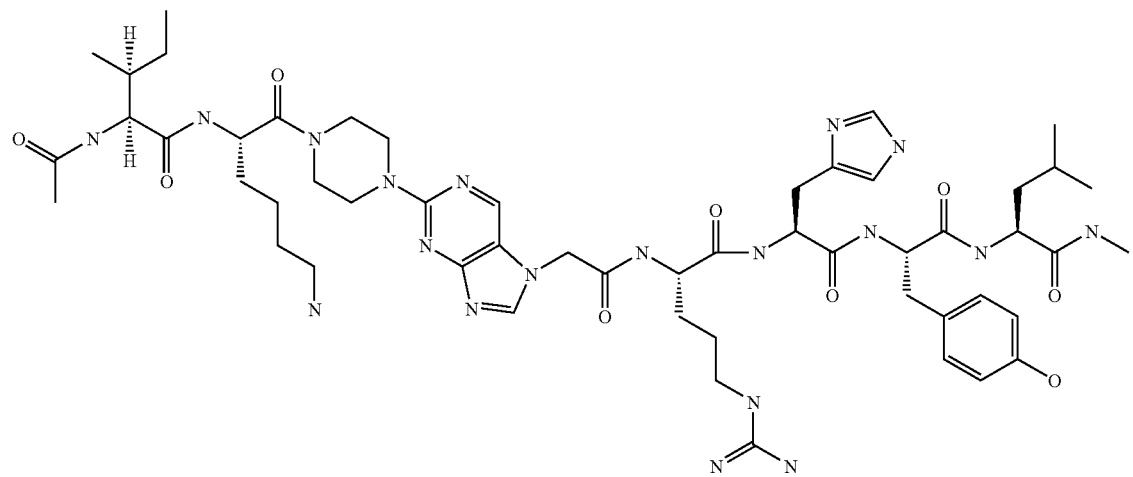

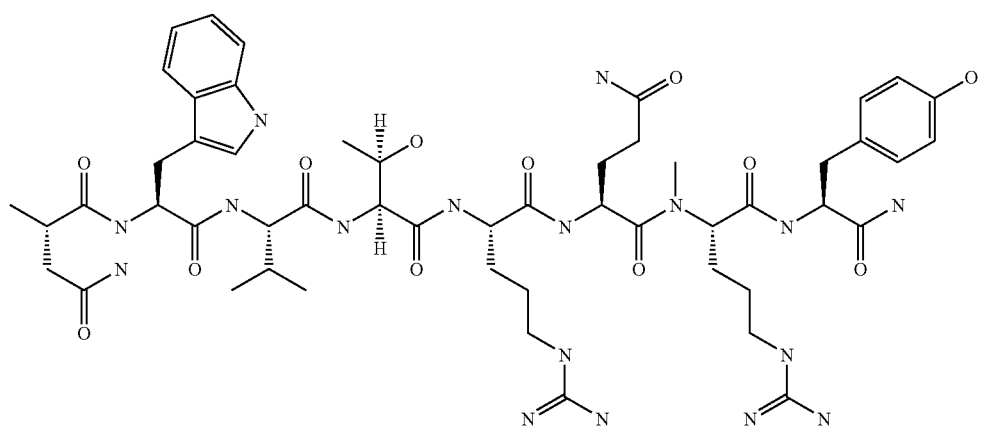

Fmoc-Linker-BHA resin (450 mg, 0.25 mmole) was prepared as described in Example 1 and was subjected to solid phase synthesis and purification by following the general procedure in Example 3, employing Fmoc-Ppa to yield 117 mg (21%) of white amorphous powder. (ES)+-LCMS m/e calculated ("calcd") for $C_{103}H_{156}N_{36}O_{21}$ 2233.22. found 2233.20.

Example 11

Preparation of Ac-Ile-Lys-Appa-Arg-His-Tyr-Leu-Asn-Trp-Val-Thr-Arg-Gln-(NMe)Arg-Tyr-NH$_2$ (SEQ ID NO: 11)

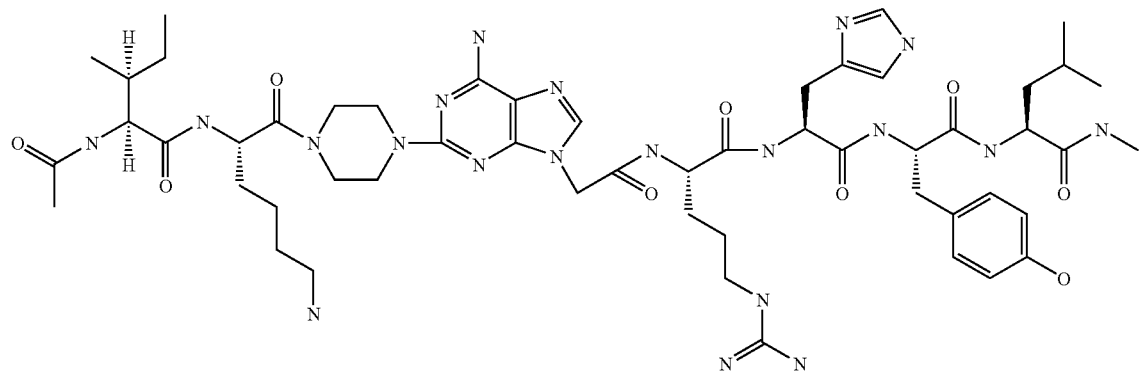

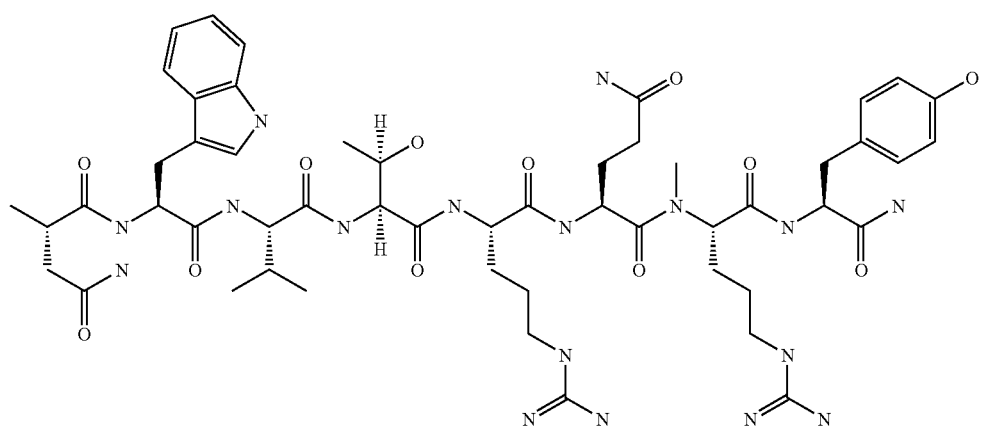

Fmoc-Linker-BHA resin (450 mg, 0.25 mmole) was prepared as described in Example 1 and was subjected to solid phase synthesis and purification by following the general procedure in Example 3, employing Fmoc-Appa to yield 98 mg (17%) of white amorphous powder. (ES)+-LCMS m/e calculated ("calcd") for C$_{103}$H$_{155}$N$_{37}$O$_{21}$ 2246.22. found 2246.20.

Example 12

Preparation of Ac-Ile-Lys-Bqa-Arg-His-Tyr-Leu-Asn-Trp-Val-Thr-Arg-Gln-(NMe)Arg-Tyr-NH$_2$ (SEQ ID NO: 12)

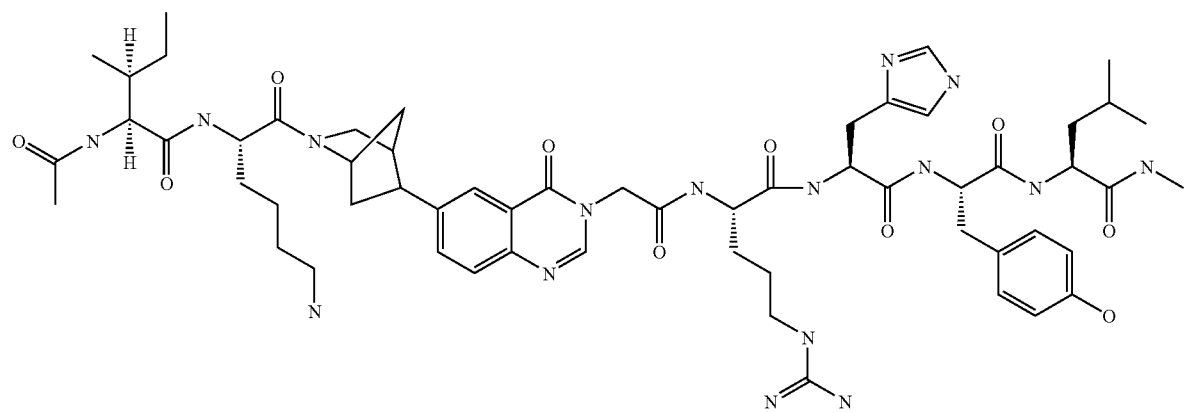

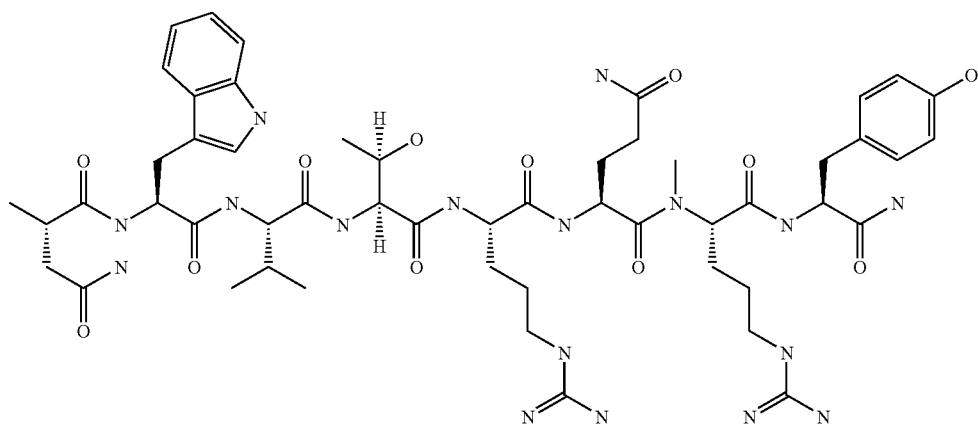

Fmoc-Linker-BHA resin (450 mg, 0.25 mmole) was prepared as described in example 1 and was subjected to solid phase synthesis and purification by following the general procedure in Example 3, employing Fmoc-Bqa to yield 79 mg (4%) of white amorphous powder. (ES)+-LCMS m/e calculated ("calcd") for $C_{108}H_{157}N_{33}O_{22}$ 2268.22. found 2268.24.

Example 13

Preparation of Ac-Ile-Lys-Pipa-Arg-His-Tyr-Leu-Asn-Trp-Val-Thr-Arg-Gln-(NMe)Arg-Tyr-NH$_2$ (SEQ ID NO: 13)

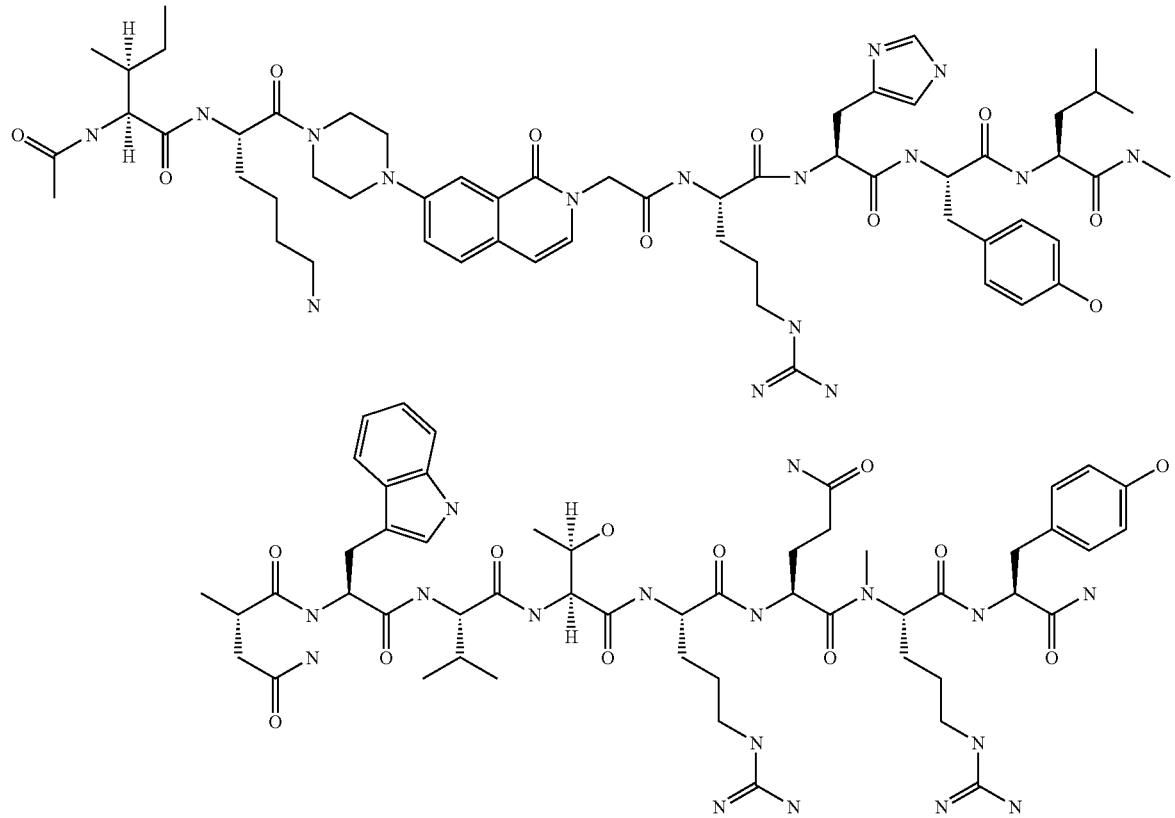

Fmoc-Linker-BHA resin (450 mg, 0.25 mmole) was prepared as described in Example 1 and was subjected to solid phase synthesis and purification by following the general procedure in Example 3, employing Fmoc-Pipa to yield 118 mg (21%) of white amorphous powder. (ES)+-LCMS m/e calculated ("calcd") for $C_{107}H_{157}N_{33}O_{22}$ 2256.22. found 2256.21.

Example 14

CAMP Agonist Assay

Cyclic AMP Assay

In this example, the following materials were used: 384-well plate; Tropix cAMP-Screen Kit; cAMP ELISA System (Applied Biosystems, Cat. #T1505; CS 20000); forskolin (Calbiochem Cat. #344270); cells: HEK293 cells expressing human NPY2-receptors; growth medium: DMEM (Gibco Cat #11995065), 10% heat inactivated FBS (Gibco Cat. #10082-147), 1% Penicillin/Streptomycin (Gibco Cat. #15140-122), 500 mg/mL G418 (Geneticin, Gibco Cat. #11811-031); plating medium: DMEM/F12 w/o phenol red (Gibco Cat #1133032), 10% heat inactivated FBS (Gibco Cat. #10082-147), 1% Penicillin/Streptomycin (Gibco Cat. #15140-122), 500 mg/mL G418 (Geneticin, Gibco Cat. #11811-031); Versene (Gibco Cat #15040066).

HEK293 cells expressing human NPY2-receptors were plated in a 384-well plate at a density of 9000 cells/well using a Multi-drop dispenser and the plates were grown overnight at 37° C. The next day, cells that reached 75-85% confluence were used in the experiment.

The media and reagents were warmed to room temperature. Before the dilutions were prepared, the stock solution of NPY2-receptor ligands and controls in dimethyl sulphoxide (DMSO, Sigma Cat. #D2650) was allowed to warm up to 32° C. for 5-10 min. The dilutions were performed using incubation media [DMEM/F12 media containing 0.5 mM 3-isobutyl-1-methylxanthine (IBMX, Calbiochem Cat #410957) and 0.5 mg/mL BSA (Sigma Cat #A8806)]. The final concentrations of DMSO and forskolin in the incubation medium were 1.1% and 5 µM, respectively.

The plating media was removed by gentle inversion of the 384-well plate on a paper towel and was replaced with incubation medium (50 µ/L well) containing various concentrations of NPY2-receptor ligands (four replicates/concentration). The plates were incubated at room temperature for 30 min. Following the 30 min treatment period, the incubation media was discarded and replaced with 50 µL/well of Assay Lysis Buffer (provided in the Tropix kit). The cells were lysed by incubating plates for 45 min @ 37° C. The lysate (20 µl) was transferred into the pre-coated antibody plates (384-well) supplied in the Tropix kit. AP conjugate (10 µL) and of anti-cAMP antibody (20 µL) was added to each well and the plates incubated on a shaker at room temperature for 1 h. The plates were washed 5 times with Wash Buffer (70 µL/well/wash) and the plates tapped dry. CSPD/Saphire-II RTU substrate/enhancer solution (30 µL/well) was added and incubated for 45 min @ room temperature. The signal in each well was measured (1 sec/well) using a Luminometer (VICTOR-V).

Example 15

Ca Flux Assay

Hek-293 cells were stably transfected with the G protein chimera Gaqi9 and the hygromycin-B resistance gene were further transfected with the human NPY2 receptor and G418 antibiotic selection. Following selection in both hygromycin-B and G418, individual clones were assayed for their response to PYY. The transfected cells were cultured in DMEM medium supplemented with 10% fetal bovine serum, 50 µg/ml hygromycin-B 2 mM glutamine, 100 U/ml penicillin, 100 µg/ml streptomycin and 250 µg/ml G418. Cells are harvested with trypsin-EDTA and counted using ViaCount reagent. The cell suspension volume is adjusted to $4.8 \times 10^5$ cells/ml with complete growth media. Aliquots of 25 µL are dispensed into 384 well Poly-D Lysine coated black/clear microplates (Falcon) and the microplates were placed in a 37° C. $CO_2$ incubator overnight. Loading Buffer (Calcium-3 Assay Kit, Molecular Devices) was prepared by dissolving the contents of one vial (Express Kit) into 1000 ml Hank's Balanced Salt Solution containing 20 mM HEPES and 5 mM probenecid. Aliquots of 25 µL of diluted dye Was dispensed into the cell plates and the plates are then incubated for 1 hour at 37° C. During the incubation, test compounds were prepared at 3.5× the desired concentration in HBSS (20 mM HEPES)/0.05% BSA/1% DMSO and transferred to a 384 well plate for use on FLIPR. After incubation, both the cell and compound plates were brought to the FLIPR and 20 µL of the diluted compounds were transferred to the cell plates by the FLIPR. During the assay, fluorescence readings were taken simultaneously from all 384 wells of the cell plate every 1.5 seconds. Five readings were taken to establish a stable baseline, and then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following addition was determined. The initial fluorescence reading from each well, prior to ligand stimulation, was used as a zero baseline value for the data from that well. The responses are expressed as % of maximal response of the positive control. The compounds of the present invention exhibited selective Neuropeptide-2 receptor activity in vitro, as demonstrated in the cAMP assay and CaFlux Assay (FLIPR). Summary of the in vitro results for Examples 3 to 13, are illustrated in Table 1 below:

TABLE 1

| Example | Sequence | Y2R EC50 (nM) FLIRR | Y2R EC50 (nM) cAMP | Y1R EC50 (nM) FLIPR | Y4R EC50 (nM) FLIPR | Y5R EC50 (nM) FLIPR |
|---|---|---|---|---|---|---|
| 3 | IKPEAPGEDASPEELNRYYASLRHYLNLVTRQRY (3-36) | 0.013 | 0.038 | 356 | 1187 | 121 |
| 4 | Ac-IK-Pqa-RHYLNWVTRQ(N-methyl)RY | 0.21 | 0.34 | >5000 | >5000 | >5000 |
| 5 | Ac-IK-Cba-RHYLNWVTRQ(N-methyl)RY | 0.51 | 1.97 | >30,000 | >30,000 | >30,000 |
| 6 | Ac-IK-Cip-RHYLNWVTRQ(N-methyl)RY | 0.14 | 0.36 | >30,000 | >30,000 | 10,669 |
| 7 | Ac-IK-HomPqa-RHYLNWVTRQ(N-methyl)RY | 0.6 | 4.35 | >9,000 | 2794 | 4935 |
| 8 | Ac-IK-Dqa-RHYLNWVTRQ(N-methyl)RY | 0.25 | 0.35 | >9,000 | >9,000 | 6026 |
| 9 | Ac-IK-Pdp-RHYLNWVTRQ(N-methyl)RY | 0.037 | 0.24 | >9,000 | >9,000 | >9,000 |
| 10 | Ac-IK-Ppa-RHYLNWVTRQ(N-methyl)RY | 0.45 | 0.12 | >5000 | >5000 | 1095 (48%) |
| 11 | Ac-IK-Appa-RHYLNWVTRQ(N-methyl)RY | 0.156 | 0.18 | >5000 | >5000 | 3297 (39%) |
| 12 | Ac-IK-Bqa-RHYLNWVTRQ(N-methyl)RY | 0.072 | 0.17 | >5000 | >5000 | 2874 (43%) |
| 13 | Ac-IK-Pipa-RHYLNWVTRQ(N-methyl)RY | 0.045 | 0.18 | >5000 | >5000 | 2338 (49%) |

(Table 1 discloses SEQ ID NOS 3-13, respectively, in order of appearance)

It is to be understood that the invention is not limited to the particular embodiments of the invention described above, as variations of the particular embodiments may be made and still fall within the scope of the appended claims.

What is claimed is:

1. A neuropeptide-2 receptor agonist of the formula (I):

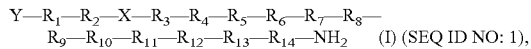 (I) (SEQ ID NO: 1), wherein:

X is (4-Aminomethyl-biphenyl-3-yl)-acetic acid (Cba), (5-piperazin-1-yl-indole-1-yl)-acetic acid (Cip), 3-(4-oxo-6-piperazin-1-yl-4H-quinazolin-3-yl)-propionic acid (HomPqa), (6-[1,4]diazepan-1-yl-4-oxo-4H-quinazolin-3-yl)-acetic acid (Dqa), (6-Oxo-2-piperazin-1-yl-1,6-dihydropurin-7-yl)-acetic acid (Pdp), (2-Piperazin-1-yl-purin-7-yl)-acetic acid (Ppa), (6-Amino-2-piperazin-1-yl-9H-purin-8-yl)-acetic acid (Appa), ((1R,4S)-6-2-Aza-bicyclo[2.2.1]hept-5-yl-4-oxo-4H-quinazolin)-acetic acid (Bqa) or, (1-Oxo-7-piperazin-1-yl-1H-isoquinolin-2-yl)-acetic acid (Pipa), Y is H or an acyl moiety, $R_1$ is Ile, Ala, (D)Ile, N-methyl Ile, Aib, 1-1Aic, 2-2 Aic, Ach or Acp, $R_2$ is Lys, Ala, (D)Lys, N-methyl lys, Nle or (Lys-Gly), $R_3$ is Arg, Ala, (D)Arg, N-methyl Arg, Phe, 3,4,5-Trifluoro Phe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D)Tyr, N-methyl Tyr, Trp, Tic, Bip, Dip, (1)Nal, (2)Nal, 3,4,5-TrifluoroPhe or 2,3,4,5,6-Pentafluoro Phe, $R_6$ is Leu, Ala, (D)Leu or N-methyl Leu, $R_7$ is Asn, Ala or (D)Asn, $R_8$ is Leu or Trp, $R_9$ is Val, Ala, (D)Val or N-methyl Val, $R_{10}$ is Thr, Ala or N-methyl Thr, $R_{11}$ is Arg, (D)Arg or N-methyl Arg, $R_{12}$ is Gln or Ala, $R_{13}$ is Arg, (D)Arg or N-methyl Arg, and $R_{14}$ is Tyr, (D) Tyr or N-methyl Tyr, Phe, (1) Nal, (2) Nal, Cha, C-alpha-methyl Tyr, or Trp, or a pharmaceutically acceptable salt thereof.

2. The neuropeptide-2 receptor agonist according to claim 1, wherein:

X is (4-Aminomethyl-biphenyl-3-yl)-acetic acid (Cba), (5-piperazin-1-yl-indole-1-yl)-acetic acid (Cip), 3-(4-oxo-6-piperazin-1-yl-4H-quinazolin-3-yl)-propionic acid (HomPqa), (6-[1,4]diazepan-1-yl-4-oxo-4H-quinazolin-3-yl)-acetic acid (Dqa), (6-Oxo-2-piperazin-1-yl-1,6-dihydropurin-7-yl)-acetic acid (Pdp), (2-Piperazin-1-yl-purin-7-yl)-acetic acid (Ppa), (6-Amino-2-piperazin-1-yl-9H-purin-8-yl)-acetic acid (Appa), ((1R,4S)-6-2-Aza-bicyclo[2.2.1]hept-5-yl-4-oxo-4H-quinazolin)-acetic acid (Bqa) or, (1-Oxo-7-piperazin-1-yl-1H-isoquinolin-2-yl)-acetic acid (Pipa), and Y is an acyl moiety (SEQ ID NO: 14).

3. The neuropeptide-2 receptor agonist according to claim 1, having formula (II):

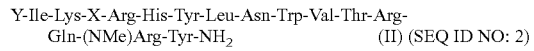 (II) (SEQ ID NO: 2)

wherein:

X is (4-Aminomethyl-biphenyl-3-yl)-acetic acid (Cba), (5-piperazin-1-yl-indole-1-yl)-acetic acid (Cip), 3-(4-oxo-6-piperazin-1-yl-4H-quinazolin-3-yl)-propionic acid (HomPqa), (6-[1,4]diazepan-1-yl-4-oxo-4H-quinazolin-3-yl)-acetic acid (Dqa), (6-Oxo-2-piperazin-1-yl-1,6-dihydropurin-7-yl)-acetic acid (Pdp), (2-Piperazin-1-yl-purin-7-yl)acetic acid (Ppa), (6-Amino-2-piperazin-1-yl-9H-purin-8-yl)-acetic acid (Appa), ((1R,4S)-6-2-Aza-bicyclo[2.2.1]hept-5-yl-4-oxo-4H-quinazolin)-acetic acid (Bqa) or, (1-Oxo-7-piperazin-1-yl-1H-isoquinolin-2-yl)-acetic acid (Pipa), and Y is an acyl moiety.

4. The neuropeptide-2 receptor agonist according to claim 1, selected from the group consisting of:

Ac-Ile-Lys-Cba-Arg-His-Tyr-Leu-Asn-Trp-Val-Thr-Arg-Gln-(NMe)Arg-Tyr-NH$_2$ (SEQ ID NO: 5),

Ac-Ile-Lys-Cip-Arg-His-Tyr-Leu-Asn-Trp-Val-Thr-Arg-Gln-(NMe)Arg-Tyr-NH$_2$ (SEQ ID NO: 6),

Ac-Ile-Lys-HomPqa-Arg-His-Tyr-Leu-Asn-Trp-Val-Thr-Arg-Gln-(NMe)Arg-Tyr-NH$_2$ (SEQ ID NO: 7),

Ac-Ile-Lys-Dqa-Arg-His-Tyr-Leu-Asn-Trp-Val-Thr-Arg-Gln-(NMe)Arg-Tyr-NH$_2$ (SEQ ID NO: 8),

Ac-Ile-Lys-Pdp-Arg-His-Tyr-Leu-Asn-Trp-Val-Thr-Arg-Gln-(NMe)Arg-Tyr-NH$_2$ (SEQ ID NO: 9),

Ac-Ile-Lys-Ppa-Arg-His-Tyr-Leu-Asn-Trp-Val-Thr-Arg-Gln-(NMe)Arg-Tyr-NH$_2$ (SEQ ID NO: 10),

Ac-Ile-Lys-Appa-Arg-His-Tyr-Leu-Asn-Trp-Val-Thr-Arg-Gln-(NMe)Arg-Tyr-NH$_2$ (SEQ ID NO: 11), Ac-Ile-Lys-Bqa-Arg-His-Tyr-Leu-Asn-Trp-Val-Thr-Arg-Gln-(NMe)Arg-Tyr-NH$_2$ (SEQ ID NO: 12) and Ac-Ile-Lys-Pipa-Arg-His-Tyr-Leu-Asn-Trp-Val-Thr-Arg-Gln-(NMe)Arg-Tyr-NH$_2$ (SEQ ID NO: 13).

5. A pharmaceutical composition, comprising a therapeutically effective amount of the neuropeptide-2 receptor agonist according to claim 1, or a salt thereof, and a pharmaceutically acceptable carrier.

* * * * *